US008460893B2

(12) United States Patent
Endo et al.

(10) Patent No.: US 8,460,893 B2
(45) Date of Patent: Jun. 11, 2013

(54) **RECOMBINANT MICROORGANISM EXPRESSING A *SECY* GENE AND METHOD OF USE THEREOF**

(75) Inventors: Keiji Endo, Tochigi (JP); Shenghao Liu, Tochigi (JP); Katsutoshi Ara, Tochigi (JP)

(73) Assignee: Kao Corporation, Tokyo (JP)

( * ) Notice: Subject to any disclaimer, the term of this patent is extended or adjusted under 35 U.S.C. 154(b) by 565 days.

(21) Appl. No.: 12/279,271

(22) PCT Filed: Feb. 15, 2007

(86) PCT No.: PCT/JP2007/000089
§ 371 (c)(1),
(2), (4) Date: Sep. 24, 2008

(87) PCT Pub. No.: WO2007/094136
PCT Pub. Date: Aug. 23, 2007

(65) Prior Publication Data
US 2009/0029417 A1 Jan. 29, 2009

(30) Foreign Application Priority Data

Feb. 16, 2006 (JP) ................................ 2006-038924
Sep. 20, 2006 (JP) ................................ 2006-254917

(51) Int. Cl.
*C12Q 1/34* (2006.01)
*C12N 1/21* (2006.01)
*C12P 21/00* (2006.01)
*C12N 15/00* (2006.01)
*C12N 9/42* (2006.01)

(52) U.S. Cl.
USPC ........ 435/18; 435/209; 435/252.31; 435/440; 435/320.1; 435/69.1

(58) Field of Classification Search
USPC ............. 435/252.3, 254.11, 209, 320.1, 69.1; 536/23.2; 530/350
See application file for complete search history.

(56) References Cited

U.S. PATENT DOCUMENTS

| 3,844,890 A | 10/1974 | Horikoshi et al. |
| 4,945,053 A | 7/1990 | Ito et al. |
| 5,726,042 A * | 3/1998 | Shivakumar et al. ........ 435/69.1 |
| 2003/0157642 A1 | 8/2003 | Coldwell et al. |
| 2004/0248279 A1 | 12/2004 | Sawada et al. |
| 2006/0057674 A1 | 3/2006 | Hintz et al. |
| 2011/0151567 A1 | 6/2011 | Liu et al. |

FOREIGN PATENT DOCUMENTS

| GB | 2095275 A | 9/1982 |
| JP | 50-28515 B | 9/1975 |
| JP | 60-23158 B | 6/1985 |
| JP | 4-190793 A | 7/1992 |
| JP | 6-030578 B2 | 4/1994 |
| JP | 2000-210081 | 8/2000 |
| JP | 2001-510046 | 7/2001 |
| JP | 2003-047490 A | 2/2003 |
| JP | 2004-173598 | * 6/2004 |
| JP | 2004-173598 A | 6/2004 |
| JP | 2005-137308 A | 6/2005 |
| JP | 2005-516613 A | 6/2005 |
| JP | 2006-296268 A | 11/2006 |
| JP | 2007-049987 A | 3/2007 |
| WO | WO 99/04006 | 1/1999 |
| WO | WO 03/066818 A2 | 8/2003 |
| WO | WO 2004/060909 A2 | 7/2004 |
| WO | WO 2004/078953 A1 | 9/2004 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Guerout-Fleury et al., Gene 180:57-64, 1996.*
Sousa et al., Microbiology 148(Pt5):1291-1303, 2002.*
Dialog File No. 351, Accession No. 535803, Derwent World Patents Index English language abstract and patent family for JP 50-28515 B (JP1975028515 B), published Sep. 16, 1975.
Dialog File No. 351, Accession No. 2497789, Derwent World Patents Index English language abstract and patent family for JP 60-23158 B (JP1985023158 B), published Jun. 6, 1985.
Dialog File No. 351, Accession No. 6043451, Derwent World Patents Index English language abstract and patent family for JP 4-190793 (JP-A-1992-190793), published Jul. 9, 1992.
Dialog File No. 351, Accession No. 10283227, Derwent World Patents Index English language abstract and patent family for JP 2000-210081, published Aug. 2, 2000.
Dialog File No. 351, Accession No. 4385807, Derwent World Patents Index English language abstract and patent family for JP 6-030578 B2 (JP-B-1994-030578), published Apr. 27, 1994.
Brigidi, P et al., "Genetic transformation of intact cells of *Bacillus subtilis* by electroporation," FEMS Microbiol Lett 55(1-2): 135-8 (Jan. 1990), Elsevier Science Publishers, Amsterdam, The Netherlands.
Chang, S et al., "High frequency transformation of *Bacillus subtilis* protoplasts by plasmid DNA," Mol Gen Genet 168(1): 111-5 (Jan. 1979), Springer-Verlag, Berlin, Germany.
Hagihara, H. et al., "Novel α-Amylase That Is Highly Resistant to Chelating Reagents and Chemical Oxidants from the Alkaliphilic *Bacillus* Isolate KSM-K38," Appl. Envir. Microbiol. 67: 1744-1750 (Apr. 2001), Am. Soc. Microbiology, Washington, DC.
Henrissat, B., "A Classification of glycosyl Hydrolases Based on Amino Acid Sequence Similarities," Biochem. J. 280: 309-316 (1991), Portland Press, London, UK.

(Continued)

*Primary Examiner* — Delia Ramirez
(74) *Attorney, Agent, or Firm* — Sterne, Kessler, Goldstein & Fox P.L.L.C.

(57) ABSTRACT

The object of the invention is to provide a microorganism which enhances productivity of cellulase and is useful for industrial production of cellulase, and to provide a method for producing cellulase by use of the microorganism. The present invention provides a recombinant microorganism produced by transferring a gene encoding cellulase to a parental microorganism which has been genetically modified so as to overexpress a *Bacillus subtilis* secY gene or a gene corresponding thereto.

13 Claims, 3 Drawing Sheets

OTHER PUBLICATIONS

Hoch, JA et al., "Transformation and Transduction in Recombination-defective Mutants of *Bacillus subtilis*," J. Bacteriol. 93: 1925-1937 (Jun. 1967), Am. Soc. Microbiology, Washington, DC.

Horinouchi, S et al., "Nucleotide sequence and functional map of pC194, a plasmid that specifies inducible chloramphenicol resistance," J. Bacteriol., 150: 815-825 (May 1982), Am. Soc. Microbiology, Washington, DC.

Horton, RM., Chapter 25 in Methods of Molecular Biology, vol. 15, PCR Protocols, Current Methods and Applications, BA White, ed., pp. 251-261, 1993, Humana Press Inc., Totowa, NJ.

Horton, RM et al., "Engineering hybrid genes without the use of restriction enzymes: gene splicing by overlap extension," Gene, 77(1): 61-8 (Apr. 1989), Elsevier Science Publishers, The Netherlands.

Itaya, M et al., "Gene-directed mutagenesis on the chromosome of *Bacillus subtilis* 168," Mol Gen Genet 223(2): 268-72 (Sep. 1990), Springer-Verlag, Secaucus, NJ.

Ito, K, et al., "A temperature-sensitive mutant of *E. coli* exhibiting slow processing of exported proteins," Cell 32(3): 789-97 (Mar. 1983), The MIT Press, Cambridge, MA.

Kobayashi, T et al., "Purification and properties of an alkaline protease from alkalophilic *Bacillus* sp. KSM-K16," Appl Microbiol Biotechnol 43(3): 473-81 (Jul. 1995), Springer-Verlag, Secaucus, NJ.

Kunst, F et al., "The complete genome sequence of the gram-positive bacterium *Bacillus subtilis*," Nature 390(6657): 249-56 (Nov. 1997), Macmillan Magazines Ltd., London, UK.

Lipman DJ et al., "Rapid and sensitive protein similarity searches," Science 227: 1435-1441 (Mar. 1985), Am. Assoc. Adv. Sci., Washington, DC.

McKenzie, T et al., "The nucleotide sequence of pUB110: some salient features in relation to replication and its regulation," Plasmid 15(2): 93-103 (Mar. 1986), Academic Press, Inc., NY.

Sanger, F. et al.., "DNA Sequencing with Chain-Terminating Inhibitors," Proc. Natl. Acad. Sci. USA 74: 5463-5467 (Dec. 1977), National Academy of Sciences, Washington, DC.

Hudspeth, D.S.S., and Vary, P.S., "*spoVG* sequence of *Bacillus megaterium* and *Bacillus subtilis*," Biochim. Biophys. Acta *1130*:229-231 (1992), plus Erratum published at Biochim. Biophys. Acta *1131*:353 (1992), and Corrigendum published at Biochim. Biophys. Acta *1216*: 509 (1993), Elsevier Publishing Company.

Zuber, P., and Losick, R., "Role of AbrB in Spo0A- and Spo0B-Dependent Utilization of a Sporulation Promoter in *Bacillus subtilis*," J. Bacteriol. *169*:2223-2230, American Society for Microbiology (1987).

International Search Report for International Application No. PCT/JP2007/000089, mailed on Apr. 3, 2007, Japanese Patent Office, Japan.

Office actions and replies from the file history of U.S. Appl. No. 12/530,135, as of Mar. 20, 2012.

Blattner, F. R., et al., "The Complete Genome Sequence of *Escherichia coli* K-12," Science 277:1453-1462, American Association for the Advancement of Science, Washington, DC (1997).

Nakamura et al., "Complementation of the protein transport defect of an *Escherichia coli* secY mutant (*secY24*) by *Bacillus subtilis* secY homologue," FEBS 273:75-78, Elsevier Science Publishers B.V., The Netherlands (1990).

Shine, J. et al., "The 3'-Terminal Sequence of *Escherichia coli* 16S Ribosomal RNA: Complementarity to Nonsense Triplets and Ribosome Binding Sites," Proc. Natl. Acad. Sci. 71:1342-1346, The National Academy of Sciences, USA (1974).

"Notice of Reasons For Rejection" for JP Patent Appl. No. 2007-102940, mailed on May 8, 2012, Japanese Patent Office, Tokyo, JP.

* cited by examiner

RECOMBINANT MICROORGANISM EXPRESSING A *SECY* GENE AND METHOD OF USE THEREOF

REFERENCE TO SEQUENCE LISTING SUBMITTED ELECTRONICALLY

The content of the electronically submitted substitute sequence listing, file name: sequencelisting_revised_ascii.txt; Size: 74,958 bytes; and Date of Creation: Mar. 15, 2011, filed herewith, is incorporated herein by reference in its entirety.

TECHNICAL FIELD

The present invention relates to a recombinant microorganism employed for production of cellulase, and to a method for producing cellulase by use of the recombinant microorganism.

BACKGROUND ART

Cellulose is a main component of the cell walls of plants, and is a typical biomass which is effectively used for, for example, making clothing, paper, and building material. Hitherto, in order to effectively use this biomass, attempts have been made to convert cellulose into sugars and further into energy-producing substances by use of a cellulose-degrading enzyme. Since alkaline cellulase derived from alkalophilic bacteria belonging to the genus *Bacillus* had been found by Horikoshi et al., (see, for example, Patent Document 1 and Non-Patent Document 1), application of cellulase to a heavy-duty detergent for clothing, which had been considered difficult, has become possible, and alkaline cellulase produced by alkalophilic bacteria belonging to the genus *Bacillus* (see, for example, Patent Documents 2 to 4) has been incorporated into detergents for clothing.

In recent years, as genetic engineering has been progressed, a variety of useful substances have been produced by use of microorganisms on an industrial scale, and enzymes for detergents have been mass-produced through genetic recombination techniques. In such industrial-scale production of useful substances by use of microorganisms, improvement of productivity thereof is one major topic of interest. In order to achieve such productivity improvement, attempts have been made to grow useful-substance-producing bacteria through mutagenesis or a similar genetic technique, and to develop host microorganisms suitable for genetic recombination.

In Gram-positive bacteria (including bacteria belonging to the genus *Bacillus* (e.g., *Bacillus subtilis*)) and Gram-negative bacteria such as *Escherichia coli*, intracellularly synthesized protein (immature secretory protein) is generally transported extracellularly via the so-called Sec pathway, which is a type of transport system. In *Bacillus subtilis*, the Sec pathway functions by, for example, SecA, which serves as a motor for extracellular release of secretory protein; three Sec proteins (SecY, SecE, and SecG), which constitute a main portion of a transport channel through which the secretory protein passes; and SecDF, which is a cofactor of the transport channel.

There have been reported an expression vector capable of overexpressing a secG gene, which encodes SecG protein (Patent Document 5), and a Gram-positive bacterium in which expression of a secG gene is altered through modification of the ribosome-binding site of the secG gene (Patent Document 6). As has been shown, for example, growth of *Bacillus subtilis* whose secG gene is disrupted is inhibited during production of a heterologous protein. As has also been reported, mutation of a secY gene in *Escherichia coli* inhibits low-temperature growth thereof or protein secretion (Non-Patent Document 2).

However, there have not yet been reported data indicating that overexpression of a secG gene or a secY gene in living cells promotes secretion or production of a target protein. In addition, it has not yet been fully elucidated how overexpression of the other genes involved in the Sec pathway affects secretion or production of a target protein.

Patent Document 1: JP-B-1975-28515
Patent Document 2: JP-B-1985-23158
Patent Document 3: JP-B-1994-030578
Patent Document 4: U.S. Pat. No. 4,945,053
Patent Document 5: JP-A-2001-510046
Patent Document 6: US Patent Application No. 2003/0157642
Non-Patent Document 1: Horikoshi & Akiba, Alkalophilic Microorganisms, Springer, Berlin (1982)
Non-Patent Document 2: Cell, 32: 789 (1983)

DISCLOSURE OF THE INVENTION

The present invention provides a recombinant microorganism produced by transferring a gene encoding cellulase to a parental microorganism which has been genetically modified so as to overexpress a *Bacillus subtilis* secY gene or a gene corresponding thereto.

The present invention also provides a method for producing cellulase, comprising employing the recombinant microorganism.

MODES FOR CARRYING OUT THE INVENTION

Figure 1:
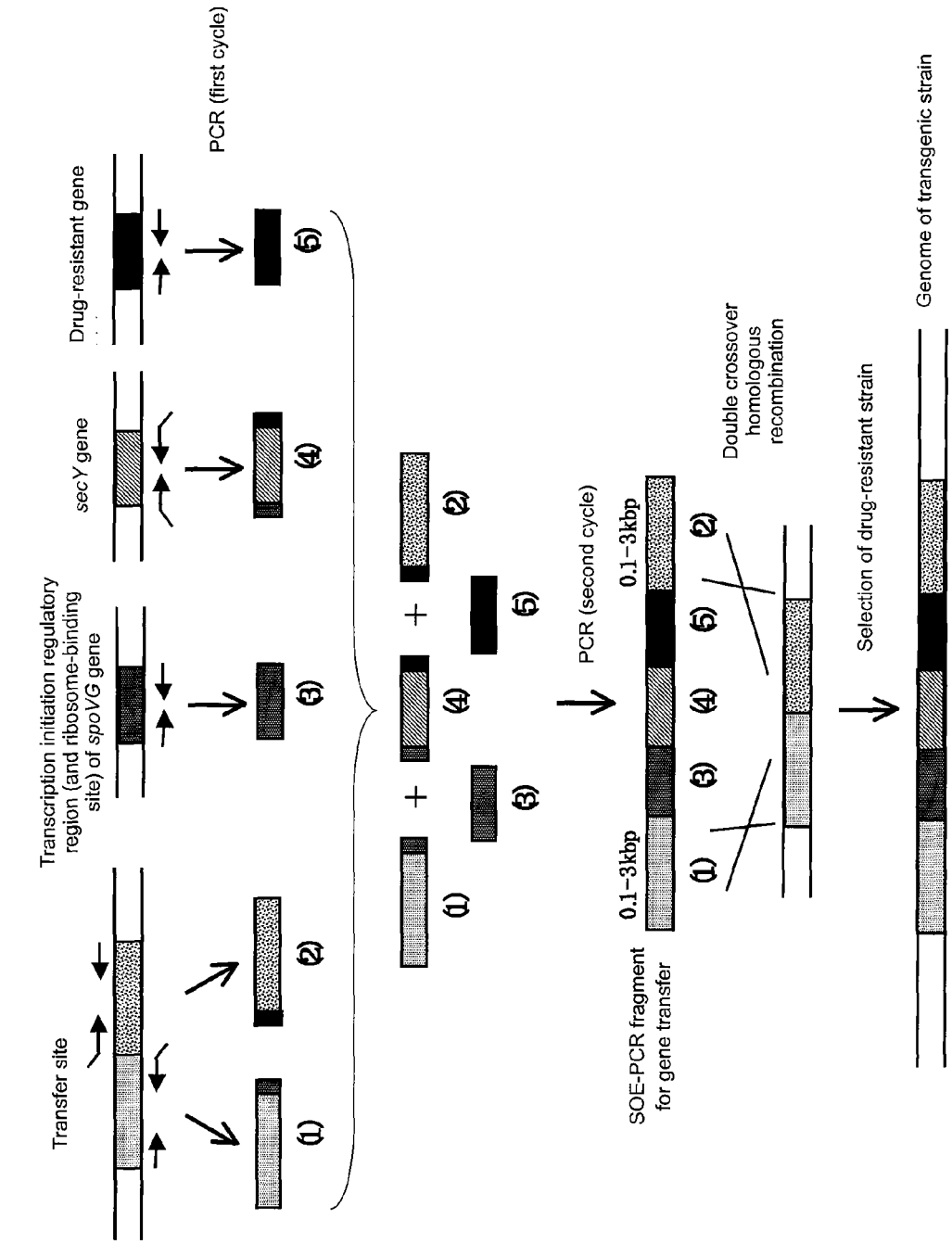
FIG. 1 schematically shows gene transfer employing a ligated nucleic acid fragment prepared through SOE-PCR.

The present invention is directed to a microorganism which enhances productivity of cellulase and is useful for industrial production of cellulase, and to a method for producing cellulase by use of the microorganism.

The present inventors have conducted studies on, among various genes encoded on the genomes of microorganisms, genes which affect the production of useful proteins or polypeptides, and have found that a microorganism which overexpresses a secY gene encoding a main component of the secretion apparatus of *Bacillus subtilis* is particularly useful for enhancing productivity of cellulase.

The recombinant microorganism of the present invention is particularly useful for the production of cellulase, and productivity of cellulase can be enhanced by use of the recombinant microorganism.

As used herein, the term "transcription initiation regulatory region" refers to a region including a promoter and a transcription initiation site; and the term "ribosome-binding site" refers to a site corresponding to the Shine-Dalgarno (SD) sequence (Proc. Natl. Acad. Sci. USA 74, 5463 (1974)) which forms a translation initiation regulatory region together with a start codon.

As used herein, the term "upstream" or "downstream" used in the context of a gene does not refer to a region as viewed from a replication origin. The term "upstream" refers a region located on the 5'-side of a gene or gene region of interest, and the term "downstream" refers a region located on the 3'-side of a gene or gene region of interest.

In the present invention, identity between amino acid sequences and that between nucleotide sequences are both determined through the Lipman-Pearson method (Science, 227, 1435 (1985)). Specifically, identity is calculated through analysis by use of a homology analysis (search homology) program of genetic information processing software Genetyx-Win (Software Development Co., Ltd.), with ktup (unit size to compare) being set to 2.

No particular limitation is imposed on the parental microorganism for constructing the recombinant microorganism of the present invention, so long as it has a *Bacillus subtilis* secY gene or a gene corresponding thereto. The parental microorganism may be a wild-type or mutant strain. Specific examples of the parental microorganism include bacteria belonging to the genus *Bacillus*, bacteria belonging to the genus *Clostridium*, and yeast. Of these, bacteria belonging to the genus *Bacillus* are preferred. *Bacillus subtilis* is more preferred, from the viewpoint that complete genomic information of this microorganism has already been obtained, and thus genetic engineering techniques and genomic engineering techniques have been established, and that the microorganism has ability to secrete a produced protein extracellularly.

The names of *Bacillus subtilis* genes and gene regions described herein conform with the *Bacillus subtilis* genome data reported in Nature, 390,249-256 (1997) and made public by JAFAN (Japan Functional Analysis Network for *Bacillus subtilis*; BSORF DB) on the Internet (bacillus.genome.ad.jp, renewed Mar. 10, 2004).

As used herein, "*Bacillus subtilis* secY gene" refers to a gene consisting of the nucleotide sequence represented by SEQ ID NO: 1, and "gene corresponding to the *Bacillus subtilis* secY gene" refers to a gene having substantially the same function as the *Bacillus subtilis* secY gene. Examples of the genes include, for example, the secY gene and a gene encoding SecY protein which have been generally identified with genomic analysis in *Bacillus licheniformis, Bacillus anthracis, Bacillus cereus, Bacillus thuringiensis*, or *Oceanobacillus iheyensis*. Some bacteria (including *Bacillus anthracis*) have two identified secY genes. Other examples of the gene corresponding to the *Bacillus subtilis* secY gene include the following genes (1) to (4).

(1) A gene consisting of a DNA fragment which consists of a nucleotide sequence having a identity of 90% or more (preferably 95% or more, more preferably 99% or more) to the nucleotide sequence represented by SEQ ID NO: 1, and which encodes a protein functionally equivalent to a protein consisting of the amino acid sequence represented by SEQ ID NO: 2.

(2) A gene consisting of a DNA fragment which hybridizes, under stringent conditions, with a DNA fragment consisting of a nucleotide sequence complementary to the nucleotide sequence represented by SEQ ID NO: 1, and which encodes a protein functionally equivalent to a protein consisting of the amino acid sequence represented by SEQ ID NO: 2. The term "stringent conditions" refers to, for example, the conditions as described in Molecular Cloning—A LABORATORY MANUAL THIRD EDITION [Joseph Sambrook, David W. Russell., Cold Spring Harbor Laboratory Press]; specifically, the condition under which hybridization is carried out by incubating a target DNA with a probe in a solution containing 6×SSC (composition of 1×SSC: 0.15 M sodium chloride, 0.015 M sodium citrate, pH 7.0), 0.5% SDS, 5×Denhardt's solution, and 100 mg/mL herring sperm DNA together at 65° C. for 8 to 16 hours.

(3) A gene consisting of a DNA fragment encoding a protein which consists of an amino acid sequence having a identity of 90% or more (preferably 95% or more, more preferably 99% or more) to the amino acid sequence represented by SEQ ID NO: 2, and which is functionally equivalent to a protein consisting of the amino acid sequence represented by SEQ ID NO: 2.

(4) A gene consisting of a DNA fragment encoding a protein which consists of an amino acid sequence represented by SEQ ID NO: 2, except that one or more amino acid residues are deleted, substituted or added, and which is functionally equivalent to a protein consisting of the amino acid sequence represented by SEQ ID NO: 2. Examples of the amino acid sequence represented by SEQ ID NO: 2, except that one or more amino acid residues are deleted, substituted or added include an amino acid sequence represented by SEQ ID NO: 2, except that one to several amino acid residues (preferably 1 to 10 amino acid residues) are deleted, substituted or added. Examples of the addition of the amino acid residue include addition of one to several amino acid residues to each end of an amino acid sequence.

As used herein, "protein functionally equivalent to a protein consisting of the amino acid sequence represented by SEQ ID NO: 2" refers to a protein which has substantially the same function as a protein encoded by the secY gene, and which can constitute a main component of the transport channel through which secretory protein passes.

The *Bacillus subtilis* secY gene or a gene corresponding thereto is overexpressed by, for example, introducing, in the genome of the parental microorganism, a transcription initiation regulatory region which functions in the parental microorganism or both the transcription initiation regulatory region and a ribosome-binding site which functions in the parental microorganism to the upstream of the *Bacillus subtilis* secY gene or the gene corresponding thereto or to the upstream of the *Bacillus subtilis* secY gene or the leading gene of an operon including the secY gene; or by introducing, to the parental microorganism, a gene fragment prepared by ligating the transcription initiation regulatory region or both the transcription initiation regulatory region and the ribosome-binding site to the upstream of the *Bacillus subtilis* secY gene or the gene corresponding thereto.

No particular limitation is imposed on the transcription initiation regulatory region which functions in a parental microorganism or both the transcription initiation regulatory region and the ribosome-binding site which function in the parental microorganism, so long as the region (or the region and site) can function in the parental microorganism serving as a host. However, preferred is the transcription initiation regulatory region or both the transcription initiation regulatory region and the ribosome-binding site located upstream of a *Bacillus subtilis* spoVG gene or aprE gene or a gene corresponding thereto; more preferably, the transcription initiation regulatory region or both the transcription initiation regulatory region and the ribosome-binding site located upstream of the *Bacillus subtilis* spoVG gene or a gene corresponding thereto.

Examples of the transcription initiation regulatory region of the *Bacillus subtilis* spoVG gene include a region which regulates transcription of the spoVG gene (gene number: BG101126) disclosed by JAFAN (Japan Functional Analysis Network for *Bacillus subtilis*; BSORF DB) on the Internet (*bacillus*.genome.ad.jp, renewed Mar. 10, 2004). Specific examples include a DNA fragment consisting of a nucleotide sequence represented by nucleotide numbers 38 to 210 of SEQ ID NO: 7; and a DNA fragment which consists of a nucleotide sequence homologous to the nucleotide sequence and which functions as the transcription initiation regulatory region of the *Bacillus subtilis* spoVG gene. Examples of the transcription initiation regulatory region and ribosome-binding site of the *Bacillus subtilis* spoVG gene include a DNA fragment consisting of a nucleotide sequence represented by nucleotide numbers 38 to 230 of SEQ ID NO: 7; and a DNA fragment which consists of a nucleotide sequence homologous to the nucleotide sequence and which functions as the transcription initiation regulatory region and ribosome-binding site of the *Bacillus subtilis* spoVG gene.

Examples of the nucleotide sequence homologous to a nucleotide sequence represented by nucleotide numbers 38 to 210 or 38 to 230 of SEQ ID NO: 7 include (A) a nucleotide sequence of a DNA fragment which hybridizes, under stringent conditions, with a DNA fragment consisting of a nucleotide sequence complementary to a nucleotide sequence represented by nucleotide numbers 38 to 210 or 38 to 230 of SEQ ID NO: 7; and (B) a nucleotide sequence having an identity of 90% or more (preferably 95% or more, more preferably 99% or more) to a nucleotide sequence represented by nucleotide numbers 38 to 210 or 38 to 230 of SEQ ID NO: 7.

The term "stringent conditions" has the same meaning as defined above.

The term "a DNA fragment functions as the transcription initiation regulatory region of the *Bacillus subtilis* spoVG gene or as the transcription initiation regulatory region and ribosome-binding site of the spoVG gene" refers to the case where, when the DNA fragment is introduced to the upstream of the *Bacillus subtilis* secY gene or a gene corresponding thereto, or upstream of the *Bacillus subtilis* secY gene or the leading gene of an operon (including the secY gene) in the genome of the parental microorganism (the leading gene is an rpsJ gene in *Bacillus subtilis*), the secY gene or a gene corresponding thereto is overexpressed, and productivity of a target protein or polypeptide is increased to an extent comparable to that in the case where the transcription initiation regulatory region of the *Bacillus subtilis* spoVG gene, or both the transcription initiation regulatory region and the ribosome-binding site of the spoVG gene are introduced to the upstream of the *Bacillus subtilis* secY gene or a gene corresponding thereto, or upstream of the *Bacillus subtilis* secY gene or the leading gene of the operon (including the secY gene) in the genome of the parental microorganism (the leading gene is an rpsJ gene in *Bacillus subtilis*).

In introduction of the transcription initiation regulatory region or both the transcription initiation regulatory region and the ribosome-binding site to the upstream of the *Bacillus subtilis* secY gene or a gene corresponding thereto in the genome of the parental microorganism or to the upstream of the *Bacillus subtilis* secY gene or the leading gene of an operon (including secY gene) in the genome of the parental microorganism (the leading gene is an rpsJ gene in *Bacillus subtilis*), the native transcription initiation regulatory region or the native transcription initiation regulatory region and ribosome-binding site of the *Bacillus subtilis* secY gene or a gene corresponding thereto, or those of the *Bacillus subtilis* secY gene or the operon (including the secY gene) in the genome of the parental microorganism may be partially or completely substituted. Alternatively, the native transcription initiation regulatory region or the native transcription initiation regulatory region and ribosome-binding site may be inserted but still remained.

Substitution of the transcription initiation regulatory region or both the transcription initiation regulatory region and the ribosome-binding site may be carried out through, for example, a known technique employing homologous recombination. Specifically, firstly, through a known technique such as SOE-PCR (SOE: splicing by overlap extension) (Gene, 77, 61, 1989), a drug-resistant gene fragment and a DNA fragment including a region upstream of the native transcription initiation regulatory region of an operon including the secY gene are ligated to the upstream of a DNA fragment including the transcription initiation regulatory region or both the transcription initiation regulatory region and the ribosome-binding site; and a DNA fragment including the entirety or a portion of the translation initiation regulatory region and structural gene region of the rpsJ gene (which is the leading gene of the operon including the secY gene), or including the entirety or a portion of the structural gene region of the rpsJ gene is ligated to the downstream of the DNA fragment including the transcription initiation regulatory region or both the transcription initiation regulatory region and the ribosome-binding site. Thus, there is prepared a DNA fragment in which the aforementioned fragments are ligated together in the following sequence: the DNA fragment including a region upstream of the native transcription initiation regulatory region of the operon including the secY gene; the drug-resistant gene fragment; the DNA fragment including the transcription initiation regulatory region or both the transcription initiation regulatory region and the ribosome-binding site; and the DNA fragment including the entirety or a portion of the translation initiation regulatory region and structural gene region of the rpsJ gene, or including the entirety or a portion of the structural gene region of the rpsJ gene. Subsequently, when the thus-prepared DNA fragment is introduced into cells of a parental microorganism through a known technique, double crossover homologous recombination occurs at two regions; i.e., a region upstream of the native transcription initiation regulatory region of the operon (including the secY gene) in the genome of the parental microorganism, and a region including the entirety or a portion of the translation initiation regulatory region and structural gene region of the rpsJ gene, or including the entirety or a portion of the structural gene region of the rpsJ gene. By use of the aforementioned drug-resistant gene as an indicator, there can be isolated a transformant in which the native transcription initiation regulatory region or both the native transcription initiation regulatory region and ribosome-binding site have been substituted with the transcription initiation regulatory region or both the transcription initiation regulatory region and the ribosome-binding site which had been introduced. Thus, the transcription initiation regulatory region or both the transcription initiation regulatory region and the ribosome-binding site, which have been introduced to the upstream of the operon (including the secY gene) in the genome of the parental microorganism, are maintained in a genetically stable manner. Specific examples of the known technique for introducing a DNA fragment for the gene transfer into a host microorganism include the competent cell transformation method (J. Bacterial. 93, 1925 (1967)), the protoplast transformation method (Mol. Gen. Genet. 168, 111 (1979)), and electroporation (FEMS Microbiol. Lett. 55, 135 (1990)). The competent cell transformation method is more preferred.

Specifically, when *Bacillus subtilis* is employed as a host for producing the microorganism of the present invention, for example, using the method described in Mol. Gen. Genet., 223, 268, 1990, substitution (through homologous recombination) can be carried out between the native transcription initiation regulatory region or the native transcription initiation regulatory region and ribosome-binding site in the operon including the secY gene and the transcription initiation regulatory region or both the transcription initiation regulatory region and the ribosome-binding site which have been introduced.

Insertion of the transcription initiation regulatory region or both the transcription initiation regulatory region and the ribosome-binding site may be carried out in a manner similar to the aforementioned substitution procedure by appropriately selecting sequences of DNA fragments to be added to each end of the fragment of the transcription initiation regulatory region or both the transcription initiation regulatory region and the ribosome-binding site. For example, a drug-resistant gene fragment and a DNA fragment including a region upstream of the native transcription initiation regulatory region of an operon including the secY gene are ligated to the upstream of the transcription initiation regulatory region to be inserted; and a DNA fragment including the entirety or a portion of the native transcription initiation regulatory region is ligated to the downstream of the transcription initiation regulatory region to be inserted. Thus, there is prepared a DNA fragment in which the aforementioned fragments and region are ligated together in the following sequence: the DNA fragment including a region upstream of the native transcription initiation regulatory region of an operon including the secY gene; the drug-resistant gene fragment; the transcription initiation regulatory region to be inserted; and the DNA fragment including the entirety or a portion of the native transcription initiation regulatory region. Subsequently, the thus-prepared DNA fragment is inserted in a host microorganism, and then the resultant transformant is isolated by use of the drug-resistant gene as an indicator. In the genome of the thus-isolated transformant, the native transcription initiation regulatory region of the operon including the secY gene and the transcription initiation regulatory region inserted are stably maintained such that the regions are adjacent to each other. Alternatively, when a DNA fragment is prepared by ligating a drug-resistant gene fragment and a DNA fragment including a region upstream of the secY gene to the upstream of the transcription initiation regulatory region to be inserted, and ligating a DNA fragment including the entirety or a portion of the secY gene to the downstream of the transcription initiation regulatory region to be inserted; and the thus-prepared DNA fragment is inserted in a host microorganism, in the resultant transformant, the transcription initiation regulatory region is stably maintained such that it is introduced immediately upstream of the secY gene.

In the present invention, no particular limitation is imposed on the upstream region in the genome of a host microorganism to which the transcription initiation regulatory region or both the transcription initiation regulatory region and the ribosome-binding site are introduced, so long as the upstream region is located upstream of the start codon of the rpsJ gene, which is the leading gene of the operon including the secY gene, or upstream of the start codon of the secY gene. However, the upstream region is preferably a region located 2000 base pairs or less (more preferably 500 base pairs or less, still more preferably 100 base pairs or less, yet still more preferably 50 base pairs or less) upstream of any of the aforementioned start codon.

In the present invention, a gene fragment prepared by ligating the transcription initiation regulatory region, or both the transcription initiation regulatory region and the ribosome-binding site to the upstream of the secY gene or a gene corresponding thereto can be introduced into a host microorganism. The gene fragment may be prepared by ligating a fragment of the transcription initiation regulatory region or both the transcription initiation regulatory region and the ribosome-binding site to a fragment of the secY gene or a gene corresponding thereto using a known technique (e.g., the restriction enzyme method, or SOE-PCR (SOE: splicing by overlap extension) (Gene, 77, 61, 1989)), and the fragments may be obtained through a known cloning technique (e.g., PCR) by using the genome of *Bacillus subtilis* or another microorganism as a template. The thus-prepared gene fragment can be introduced into the chromosome of a host cell by homologous recombination between the chromosome and the nucleic acid fragment introduced into the cell through a known transformation technique.

So long as the nucleotide sequence of the secY gene or a gene corresponding thereto which is introduced into a host microorganism is identified per se, the nucleotide sequence is not necessarily identical to that of the secY gene or a gene corresponding thereto intrinsic in the microorganism. So long as the nucleotide sequence of the transcription initiation regulatory region or both the transcription initiation regulatory region and the ribosome-binding site which is (are) introduced into a host microorganism (e.g., the transcription initiation regulatory region or the transcription initiation regulatory region and ribosome-binding site of the *Bacillus subtilis* spoVG gene) is identified per se, the nucleotide sequence is not necessarily identical to that intrinsic in the microorganism. Examples of the technique for introducing a nucleic acid fragment into a host include the competent cell transformation method, the protoplast transformation method, and electroporation. The competent cell transformation method is more preferred.

Such a fragment may be introduced into the cytoplasm by use of a vector (e.g., plasmid). As described in the Examples hereinbelow, since such a fragment exhibits a sufficient effect of producing a target protein or polypeptide through introduction of one copy of the fragment per cell, when the fragments are introduced by use of plasmids, removal of a portion of the plasmids during culturing for producing the protein or polypeptide is less likely to affect the productivity.

The region of the chromosome of a host into which such a fragment is introduced is preferably a region in a nonessential gene, or a region in a nongenic region upstream of a nonessential gene. Specific examples include a region in an aprE gene, a sacB gene, an nprE gene, an amyE gene, or a ybxG gene; and a region in a nongenic region upstream thereof. A region in an amyE gene, or a region in a nongenic region upstream of a ybxG gene is preferred. As used herein, the term "nonessential gene" refers to a gene which, even when disrupted, allows a host to survive at least under certain conditions. Deletion of the entirety or a portion of a nonessential gene or a nongenic region upstream of the gene, which would otherwise occur in association with the fragment introduction, does not cause any problem.

In the present invention, in addition to the aforementioned overexpression of the *Bacillus subtilis* secY gene or a gene corresponding thereto, other genes of *Bacillus subtilis* involved in the Sec pathway (e.g., the secE gene) or genes involved in a function other than the Sec pathway may be overexpressed, or one or more genes may be inactivated or deleted, so long as such overexpression, inactivation, or deletion does not affect enhancement of productivity of cellulase. The "inactivation or deletion of a gene" encompasses substitution or deletion of the entirety or a portion of the nucleotides of the gene, and insertion of a nucleotide(s) in the gene.

Next will be described in more detail a method for introducing (by double crossover), into the genome of a host. In the method, a gene fragment is used which has been prepared by ligating a transcription initiation regulatory region (or the transcription initiation regulatory region and ribosome-binding site) of the spoVG gene to the upstream of the secY gene, the method employing a DNA fragment prepared through SOE-PCR (SOE: splicing by overlap extension) (Gene, 77, 61, 1989). However, in the present invention, the method for introduction of a gene fragment is not limited to the below-described method.

The DNA fragment employed in this method for the gene transfer is a DNA fragment including: (1) a fragment (about 0.1 to about 3 kb, preferably 0.4 to 3 kb) to be located upstream adjacent to the introduction site in the genome of a host (hereinafter "fragment (1)"); (2) a fragment (about 0.1 to about 3 kb, preferably 0.4 to 3 kb) to be located downstream adjacent to the introduction site (hereinafter "fragment (2)"); (3) a fragment including the transcription initiation regulatory region or the transcription initiation regulatory region and ribosome-binding site of the spoVG gene (hereinafter "fragment (3)"); (4) a fragment of the secY gene (hereinafter "fragment (4)"); and (5) a fragment of a drug-resistant marker gene (e.g., a chloramphenicol-resistant gene) (hereinafter "fragment (5)"), wherein fragments (3), (4), and (5) are sequentially inserted between fragments (1) and (2). In the first PCR, the aforementioned five fragments (i.e., fragments (1) to (5)) are prepared. The primers employed in this step is, for example, those designed so that an upstream 10-30 base pair sequence of fragment (3) is attached to the downstream end of fragment (1); a downstream 10-30 base pair sequence of fragment (3) is attached to the upstream end of fragment (4); an upstream 10-30 base pair sequence of fragment (5) is attached to the downstream end of fragment (4); and a downstream 10-30 base pair sequence of fragment (5) is attached to the upstream side of fragment (2) (FIG. 1).

Subsequently, by using the five PCR fragments prepared in the first PCR as templates, the second PCR is carried out by use of an upstream primer of fragment (1) and a downstream primer of fragment (2). This step causes annealing of fragment (3) with the sequence of fragment (3) attached to the downstream end of fragment (1); annealing of fragment (3) with the sequence of fragment (3) attached to the upstream end of fragment (4); annealing of fragment (5) with the sequence of fragment (5) attached to the downstream end of fragment (4); and annealing of fragment (5) with the sequence of fragment (5) attached to the upstream end of fragment (2). Thus, through PCR amplification, there can be obtained a DNA fragment including fragments (1) to (5), wherein fragment (1), fragment (3), fragment (4), fragment (5), and fragment (2) are sequentially ligated (FIG. 1).

The aforementioned PCR may be carried out under typical conditions described in literatures (see, for example, PCR Protocols. Current Methods and Applications, Edited by B. A. White, Humana Press, pp. 251, 1993, Gene, 77, 61, 1989) by use of a primer set shown in Table 1 and a generally used enzyme kit for PCR (e.g., Pyrobest DNA Polymerase, product of Takara Shuzo).

When the thus-obtained DNA fragment for the gene transfer is introduced into cells through the competent method or a similar method, intracellular genetic recombination occurs in homologous regions which are present upstream and downstream of the target site for gene transfer on the homologous genome. Thus, cells, into which the gene fragment prepared by ligating the transcription initiation regulatory region (or the transcription initiation regulatory region and ribosome-binding site) of the spoVG gene to the upstream of the secY gene has been introduced, can be selectively separated by use of a drug-resistant marker. In selective separation by use of a drug-resistant marker, for example, colonies which have grown on an agar medium containing chloramphenicol are separated, followed by selection of cells in which introduction of the gene fragment in the genome is confirmed with PCR employing the genome as a template or with similar techniques. No particular limitation is imposed on the aforementioned drug-resistant marker gene, so long as it can be employed for cell selection by use of a common antibiotic. Examples of the drug-resistant marker gene which may employed include, in addition to a chloramphenicol-resistant gene, drug-resistant marker genes such as an erythromycin-resistant gene, a neomycin-resistant gene, a spectinomycin-resistant gene, a tetracycline-resistant gene, and a brasticidin S-resistant gene.

The recombinant microorganism of the present invention can be produced by transferring a gene encoding cellulase of interest into the thus-genetically modified microorganism. As used herein, "gene encoding cellulase" encompasses a gene which is not intrinsic to the microorganism (i.e., a foreign gene) as well as a gene intrinsic to the microorganism.

In the present invention, examples of the cellulase of interest include cellulases belonging to family 5 in the classification of polysaccharide hydrolase (Biochem. J., 280, 309, 1991); preferably, cellulases derived from microorganisms, more preferably cellulases derived from the genus *Bacillus*. Specific examples include alkaline cellulases derived from *Bacillus* sp. KSM-S237 strain (FERM BP-7875) and *Bacillus* sp. KSM-64 strain (FERM BP-2886). Examples of more preferred cellulases include alkaline cellulase derived from a bacterium belonging to the genus *Bacillus* and having an amino acid sequence represented by amino acid residue numbers 1 to 795 of SEQ ID NO: 4; alkaline cellulase derived from a bacterium belonging to the genus *Bacillus* and having an amino acid sequence represented by amino acid residue numbers 1 to 793 of SEQ ID NO: 6; and cellulase having an amino acid sequence having an identity of 70% or higher (preferably 80% or higher, more preferably 90% or higher, still more preferably 95% or higher, yet still more preferably 98% or higher) to any of the aforementioned amino acid sequences.

A cellulase-encoding gene to be transferred to the microorganism of the present invention preferably has, on the upstream thereof, one or more regulatory regions relating to transcription, translation, and secretion of the gene (specifically, one or more regions selected from among a transcription initiation regulatory region including a promoter and a transcription initiation site; a translation initiation regulatory region including a ribosome-binding site and a start codon; and a secretion signal peptide region) which are properly ligated to the gene. More preferably, the following three regions; i.e., the transcription initiation regulatory region, the translation initiation regulatory region, and the secretion signal region, are ligated to the cellulase gene. More preferably, the secretion signal peptide region is derived from a cellulase gene of a bacterium belonging to the genus *Bacillus*; the transcription initiation regulatory region and the translation initiation regulatory region are each derived from a 0.6 to 1 kb region upstream of the cellulase gene; and these regions are properly ligated to the cellulase gene of interest. For example, preferably, a transcription initiation regulatory region, a translation initiation regulatory region, and a secretion signal peptide region of a cellulase gene derived from a bacterium belonging to the genus *Bacillus* disclosed in, for example, JP-A-2000-210081 or JP-A-1992-190793; i.e., a cellulase gene derived from KSM-S237 strain (FERM BP-7875) or KSM-64 strain (FERM BP-2886), are properly ligated to a structural gene of cellulase. More specifically, preferably, a structural gene of cellulase is properly ligated to a DNA fragment consisting of a nucleotide sequence represented by nucleotide numbers 1 to 659 of SEQ ID NO: 3; a DNA fragment consisting of a nucleotide sequence represented by nucleotide numbers 1 to 696 of SEQ ID NO: 5; a DNA fragment consisting of a nucleotide sequence having an identity of 70% or higher (preferably 80% or higher, more preferably 90% or higher, still more preferably 95% or higher, yet still more preferably 98% or higher) to any of the aforementioned nucleotide sequences; or a DNA fragment consisting of a nucleotide sequence obtained through partial modification (deletion, substitution, or addition) of any of the aforementioned nucleotide sequences. As used herein, "DNA fragment having a nucleotide sequence obtained through partial modification (deletion, substitution, or addition) of any of the aforementioned nucleotide sequences" refers to a DNA fragment in which a portion of any of the aforementioned nucleotide sequences has undergone deletion, substitution, or addition, but which maintains functions relating to transcription and translation of the gene, and secretion.

Transfer of such a gene encoding cellulase of interest may be carried out through, for example, (1) transfer by use of a vector, or (2) insertion in the genome of a host. When (1) gene transfer by use of a vector is carried out, a vector containing a gene encoding a target protein or polypeptide is transferred into the host with an appropriate transformation technique, wherein the gene has "one or more regulatory regions relating to transcription, translation, and secretion of the gene (specifically, one or more regions selected from among a transcription initiation regulatory region including a promoter and a transcription initiation site; a translation initiation regulatory region including a ribosome-binding site and a start codon; and a secretion signal peptide region)" properly ligated upstream thereto, and the appropriate transformation technique includes the competent cell transformation method, the protoplast transformation method and electroporation. No particular limitation is imposed on the vector employed, so long as it is an appropriate carrier nucleic acid molecule to introduce a target gene into a host for amplification and expression of the gene. Examples of the vector include plasmid; artificial chromosomes such as YAC and BAC; vectors using transposon; and cosmid. Examples of the plasmid include pUB110 and pHY300PLK.

(2) Insertion in the genome of a host may be carried out through, for example, homologous recombination. Specifically, a DNA fragment prepared by ligating a cellulase-encoding gene to a portion of a chromosomal region to be introduced is transferred into cells of a microorganism, to thereby allow homologous recombination to occur in a portion of the chromosomal region. Thus, the gene can be integrated into the genome of the microorganism. No particular limitation is imposed on the chromosomal region to which the gene is transferred, but the chromosomal region is preferably a nonessential gene region, or a nongenic region upstream of a nonessential gene region.

The thus-prepared recombinant microorganism is particularly useful for the production of cellulase, and enhances productivity of cellulase of interest.

Production of cellulase by use of the recombinant microorganism of the present invention may be carried out in such a manner that cells of the microorganism are inoculated into a culture medium containing assimilable carbon sources, nitrogen sources, and other essential components; the cells are cultured through a common microorganism culturing method; and, after completion of culturing, the resultant protein or polypeptide is collected and purified.

EXAMPLES

In the Examples described hereinbelow, DNA fragment amplification was carried out through polymerase chain reaction (PCR) by use of GeneAmp PCR System (product of Applied Biosystems), and Pyrobest DNA Polymerase (product of Takara Bio Inc.) and reagents attached thereto. Specifically, PCR was carried out by use of a reaction mixture (total: 50 µL) containing appropriately diluted template DNA (1 µL), a sense primer (20 µmol), an antisense primer (20 µmol), and Pyrobest DNA Polymerase (2.5 U). PCR was carried out through 30 cycles of reaction, each cycle consisting of the three steps of thermal treatment (98° C.×10 seconds, 55° C.×30 seconds, and 72° C.×1 to 5 minutes, which varies depending on a target amplification product; approximately, 1 minute for 1 kb), followed by treatment of the reaction mixture at 72° C. for five minutes.

The names of genes and gene regions employed in the below-described Examples conform with the *Bacillus subtilis* genome data reported in Nature, 390, 249-256 (1997) and made public by JAFAN (Japan Functional Analysis Network for *Bacillus subtilis*; BSORF DB) on the Internet (bacillus.genome.ad.jp, renewed Mar. 10, 2004).

Transformation of *Bacillus subtilis* was carried out as described below.

Specifically, cells of *Bacillus subtilis* were inoculated into an SPI medium (0.20% ammonium sulfate, 1.40% dipotassium hydrogenphosphate, 0.60% potassium dihydrogenphosphate, 0.10% trisodium citrare dihydrate, 0.50% glucose, 0.02% casamino acid (Difco), 5 mM magnesium sulfate, 0.25 µM manganese chloride, and 50 µg/mL tryptophan), followed by shake culturing at 37° C. until the growth degree (OD600) reached about 1. After completion of shake culturing, an aliquot of the resultant culture liquid was inoculated into a 9-fold amount of an SPII medium (0.20% ammonium sulfate, 1.40% dipotassium hydrogenphosphate, 0.60% potassium dihydrogenphosphate, 0.10% trisodium citrare dihydrate, 0.50% glucose, 0.01% casamino acid (Difco), 5 mM magnesium sulfate, 0.40 µM manganese chloride, and 5 µg/mL tryptophan), followed by further shake culturing until the growth degree (OD600) reached about 0.4, to thereby prepare competent cells of *Bacillus subtilis*. Subsequently, a solution containing a DNA fragment (e.g., SOE-PCR reaction mixture) (5 µL) was added to the thus-prepared competent cell suspension (SPII-medium-based culture liquid) (100 µL), followed by shake culturing at 37° C. for one hour. Thereafter, the entire amount of the resultant culture liquid was smeared on an LB agar medium (1% triptone, 0.5% yeast extract, 1% NaCl, and 1.5% agar) containing an appropriate drug, followed by stationary culturing at 37° C. Thereafter, the thus-grown colonies were separated as a transformant, and the genome of the thus-obtained transformant was extracted. PCR employing the genome as a template indicated that a target genomic modification had been achieved.

Example 1

Construction of secY-Gene-Overexpressing Strain

Figure 2:
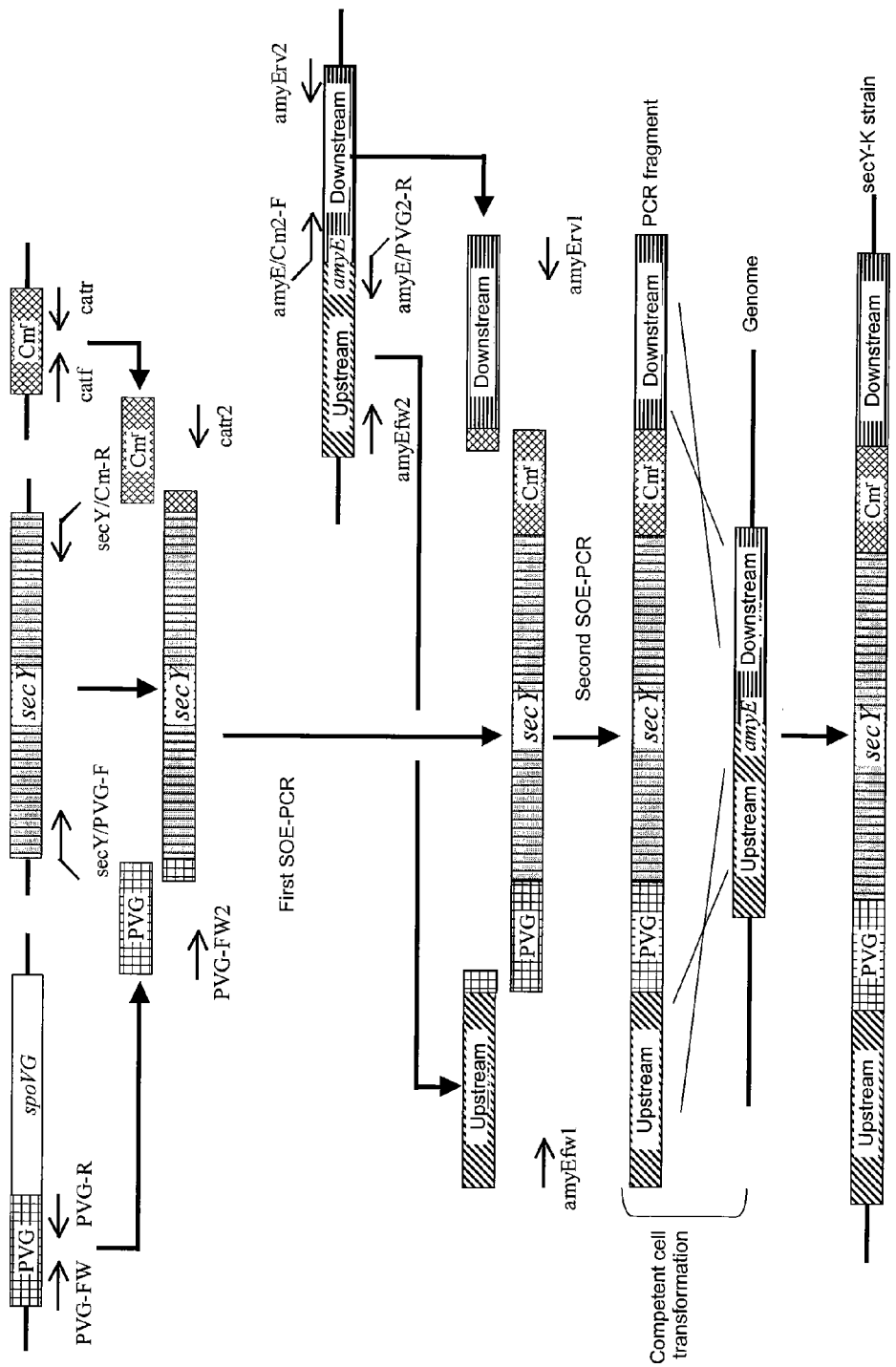
FIG. 2 schematically shows an exemplified method for preparing, through SOE-PCR, a DNA fragment for transfer of a secY gene, in which the transcription initiation regulatory region and ribosome-binding region of a spoVG gene are ligated to the secY gene, and for transferring the secY gene to the chromosome of a host by use of the DNA fragment.

A mutant strain overexpressing the secY gene was constructed as follows (see FIG. 2). By using, as a template, genomic DNA extracted from *Bacillus subtilis* 168 strain, and two primer sets (PVG-FW and PVG-R, and secY/PVG-F and secY/Cm-R) shown in Table 1, a 0.2 kb fragment (A) including the transcription initiation regulatory region and ribosome-binding site of the spoVG gene, and a 1.3 kb fragment (B) including the secY gene were amplified through PCR. By use of plasmid pC194 (J. Bacteriol. 150 (2), 815 (1982)) as a template, and a primer set (catf and catr) shown in Table 1, a 0.9 kb fragment (C) including a chloramphenicol (Cm)-resistant gene was amplified through PCR. Subsequently, SOE-PCR was carried out by use of the thus-obtained three fragments (A), (B), and (C) in combination as templates, and by use of a primer set (PVG-FW2 and catr2) shown in Table 1, to thereby prepare a 2.2 kb DNA fragment (D) in which the three fragments (A), (B), and (C) were ligated in this sequence; the transcription initiation regulatory region and ribosome-binding site of the spoVG gene were ligated to the upstream of the secY gene so that the start codon of the secY gene was located at which the start codon of the spoVG gene had been located; and the Cm-resistant gene was ligated to the downstream of the secY gene. Subsequently, by using, as a template, genomic DNA extracted from *Bacillus subtilis* 168 strain, and two primer sets (amyEfw2 and amyE/PVG2-R, and amyE/Cm2-F and amyErv2) shown in Table 1, a 1.0 kb fragment (E) including the 5'-side region of the amyE gene, and a 1.0 kb fragment (F) including the 3'-side region of the amyE gene were amplified through PCR. Subsequently, SOE-PCR was carried out by use of the thus-obtained three fragments (E), (F), and (D) in combination as templates, and by use of a primer set (amyEfw1 and amyErv1) shown in Table 1, to thereby prepare a DNA fragment (G) (total length of 4.2 kb) in which the three fragments (E), (D), and (F) were ligated in this sequence; and the 2.2 kb DNA fragment (in which the secY gene was ligated to the downstream of the transcription initiation regulatory region and ribosome-binding site of the spoVG gene, and the chloramphenicol-resistant gene was ligated to the downstream of the secY gene) was inserted into the amyE gene. *Bacillus subtilis* 168 strain was transformed through the competent cell method by use of the thus-obtained 4.2 kb DNA fragment (G), and colonies grown in an LB agar medium containing chloramphenicol (10 μg/mL) were separated as a transformant. PCR employing, as a template, genomic DNA extracted from the transformant, and two primer sets (amyEfw2 and secY/Cm-R, and secY/PVG-F and amyErv2) shown in Table 1 indicated that 2.5 kb and 3.1 kb DNA fragments were amplified, and that the DNA fragment in which the secY gene was ligated to the downstream of the transcription initiation regulatory region and ribosome-binding site of the spoVG gene was inserted into the amyE gene site in the genome of *Bacillus subtilis* 168 strain. The thus-obtained strain was denominated "secY-K strain."

TABLE 1

| Primer | Sequence (5'-3') | SEQ ID NO. |
| --- | --- | --- |
| PVG-FW | GTTAGTCGAGATCGAAGTTA | 8 |
| PVG-R | AGTAGTTCACCACCTTTTCC | 9 |
| secY/PVG-F | GGAAAAGGTGGTGAACTACTATGTTGTTTAAAACAATCTCCAA | 10 |
| secY/Cm-R | ATGGGTGCTTTAGTTGAAGACTAGTTTTTCATAAATCCAC | 11 |
| catf | CAACTAAAGCACCCATTAG | 12 |
| catr | CTTCAACTAACGGGGCAG | 13 |
| PVG-FW2 | TAAGAAAAGTGATTCTGGGA | 14 |
| catr2 | CTCATATTATAAAAGCCAGTC | 15 |
| amyEfw2 | GGAGTGTCAAGAATGTTTGC | 16 |
| amyE/PVG2-R | TCCCAGAATCACTTTTCTTAATCATCGCTCATCCATGTCG | 17 |
| amyE/Cm2-F | GACTGGCTTTTATAATATGAGGTTTAGGCTGGGCGGTGATA | 18 |
| amyErv2 | TCAATGGGAAGAGAACC | 19 |
| amyEfw1 | TCAAAACCTCTTTACTGCCG | 20 |
| amyErv1 | CACGTAATCAAAGCCAGGCT | 21 |
| 237UB1 | TTGCGGATCCAACAGGCTTATATTTAGAGGAAATTTC | 22 |
| 237DB1 | TTGCGGATCCAACAACTCTGTGTCCAGTTATGCAAG | 23 |
| secE/Y-F2 | GTGGATTTATGAAAAACTAGTTGTGGAGGTCTTTTACATG | 24 |
| secE/Ne-R | TATTTTATAAACTCATTCCCCATTATTCAACTATTAAACG | 25 |
| amyE/Nm-F | TGACCTCTAATAATTGTTAAGTTTAGGCTGGGCGGTGATA | 26 |
| rneof | GGGAATGAGTTTATAAAAT | 27 |
| repUr-Nm | TTCCTAAGCATCATGGTCTCACTTTTCCACTTTTTGTCTTG | 28 |

TABLE 1-continued

| Primer | Sequence (5'-3') | SEQ ID NO. |
|---|---|---|
| NmUf-rep | GTGAGACCATGATGCTTAGGAAGACGAGTTATTAATAGC | 29 |
| Nmr | TTAACAATTATTAGAGGTCA | 30 |
| secY-F2 | TTGTTTAAAACAATCTCCAA | 31 |
| secG/PVGf | GGAAAAGGTGGTGAACTACTTGAGTCTGGAGGTGTATGGG | 32 |
| secG/Ne-R | TATTTTATAAACTCATTCCCCCCTATAGGATATAAGCAAG | 33 |
| S237ppp-F2 (BamHI) | CCCGGATCCAACAGGCTTATATTTA | 34 |
| S237ppp-R2 (ALAA) | TTCAATCCATCTGCTGCAAGAGCTGCCGG | 35 |
| K38matu-F2 (ALAA) | GCTCTTGCAGCAGATGGATTGAACGGTACG | 36 |
| SP64K38-R (XbaI) | TTGGTCTAGACCCCAAGCTTCAAAGTCGTA | 37 |

Example 2

Evaluation of Secretion/Production of Alkaline Cellulase

As described below, heterologous protein productivities of the secY-K strain obtained in Example 1 and *Bacillus subtilis* 168 strain (control) were evaluated on the basis of productivity of alkaline cellulase derived from a bacterium belonging to the genus *Bacillus* having the amino acid sequence represented by SEQ ID NO: 4. Specifically, a fragment (3.1 kb) of an alkaline cellulase gene derived from *Bacillus* sp. KSM-S237 strain (FERM BP-7875) (JP-A-2000-210081) was amplified by use of a primer set (237UB1 and 237 DB1) shown in Table 1, and then treated with the restriction enzyme BamHI. The thus-treated fragment was inserted into the restriction enzyme BamHI cleavage site in a shuttle vector pHY300PLK, to thereby prepare a recombinant plasmid pHY-S237. The plasmid pHY-S237 was introduced into the secY-K strain or *Bacillus subtilis* 168 strain (control) through the protoplast transformation method. Cells of the thus-obtained recombinant strain were shake-cultured in an LB medium (10 mL) overnight at 37° C. The resultant culture liquid (0.05 mL) was inoculated into a 2×L-maltose medium (50 mL) (2% tryptone, 1% yeast extract, 1% NaCl, 7.5% maltose, 7.5 ppm manganese sulfate 4-5 hydrate, and 15 ppm tetracycline), followed by shake culturing at 30° C. for three days. After completion of culturing, cells were removed through centrifugation, and alkaline cellulase activity of the culture supernatant was determined, to thereby calculate the amount of alkaline cellulase extracellularly secreted from the cells during culturing.

For determination of cellulase activity, 0.4 mM p-nitrophenyl-β-D-cellotrioside (product of Seikagaku Corporation) (50 µL) was added to and mixed with a sample solution (50 µL) appropriately diluted with 1/7.5 M phosphate buffer (pH 7.4, product of Wako Pure Chemical Industries, Ltd.), and the amount of p-nitrophenol released during reaction at 30° C. was quantitatively determined on the basis of a change in absorbance at 420 nm (OD 420 nm). The amount of enzyme required for release of 1 µmol of p-nitrophenol for one minute was defined as 1 U.

As is clear from the alkaline cellulase activity data shown in Table 2, when the secY-K strain is employed as a host, secretion/production of alkaline cellulase was enhanced, as compared with the case where the control 168 strain (wild-type strain) was employed. Conceivably, this enhancement of secretion/production of alkaline cellulase resulted from an increase in secretion efficiency of cellulase by virtue of enhancement of expression of the secY gene in the secY-K strain (as compared with the case of the wild-type strain), and an increase in amount of SecY protein serving as a secretion apparatus.

TABLE 2

| Strain name | Overexpressed gene | Amount of secreted/produced alkaline cellulase (relative value) |
|---|---|---|
| secY-K strain | secY | 117 |
| 168 strain | None | 100 |

Comparative Example 1

Construction of Another-Sec-Gene-Overexpressing Strain-1

Figure 3:
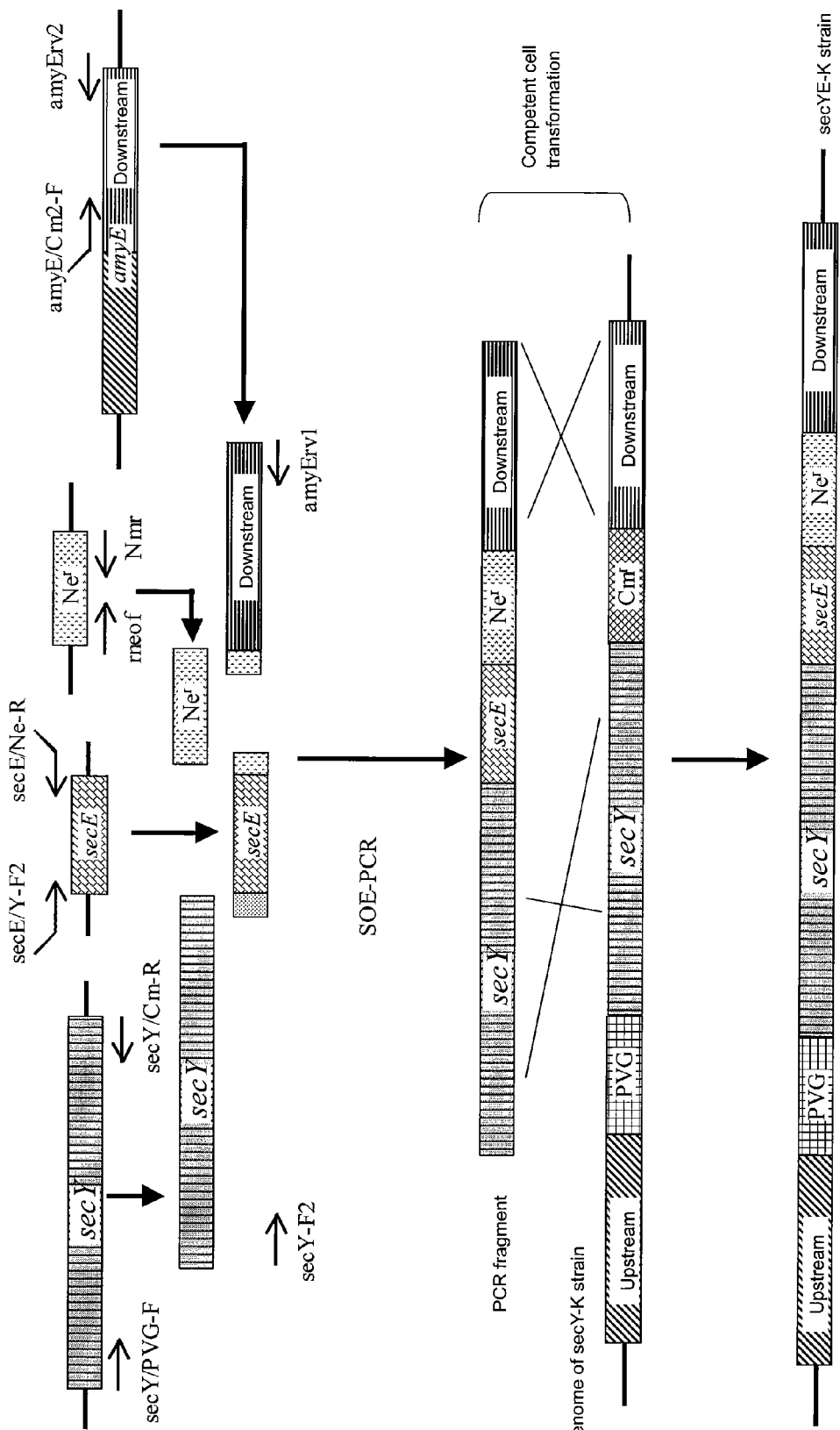
FIG. 3 schematically shows a method for preparing, through SOE-PCR, a DNA fragment for gene transfer in which a secE gene is ligated to the downstream of a secY gene introduced into an amyE gene site so that both the secY gene and the secE gene are transcribed, and for transferring the secY gene and the secE gene to the chromosome of a host by use of the DNA fragment.

A strain overexpressing both the secY gene and the secE gene was constructed as follows (see FIG. 3). Specifically, by using, as a template, genomic DNA extracted from *Bacillus subtilis* 168 strain, and three primer sets (secE/Y-F2 and secE/Ne-R, secY/PVG-F and secY/Cm-R, and amyE/Nm-F and amyErv2) shown in Table 1, a 0.2 kb fragment (H) including the secE gene and the ribosome-binding site thereof, a 1.3 kb fragment (I) including the secY gene, and a 1.0 kb fragment (J) including the 3'-side region of the amyE gene were amplified through PCR. Separately, a 0.4 kb fragment including the promoter region of the repU gene was prepared by using a primer set (rneof and repUr-Nm) shown in Table 1, and plasmid pUB110 (Plasmid 15, 93 (1986)) as a template; and a 0.8 kb fragment including the structural gene region of a neomycin-resistant gene was prepared by using a primer set (NmUf-rep and Nmr) shown in Table 1, and plasmid pUB110 as a template. SOE-PCR was carried out by use of the thus-prepared 0.4 kb and 0.8 kb fragments in combination as templates, and by use of a primer set (rneof and Nmr) shown in Table 1, to thereby prepare a 1.2 kb neomycin-resistant cassette fragment (K). Subsequently, SOE-PCR was carried out by use of the thus-prepared four fragments (H), (I), (J), and (K) in combination as templates, and by use of a primer set (secY-F2 and amyErv1) shown in Table 1, to thereby prepare a DNA fragment (L) (total length of 3.7 kb) in which the four fragments (I), (H), (K), and (J) were ligated in this sequence; the secE gene and the ribosome-binding site thereof were ligated to the downstream of the secY gene; and the neomycin-resistant cassette and the 3'-side region of the amyE gene were ligated to the downstream of the secE gene. The secY-K strain constructed in Example 1 was transformed through the competent cell method by use of the thus-obtained 3.7 kb DNA fragment (L), and colonies grown in an LB agar medium containing neomycin (10 μg/mL) were separated as a transformant. PCR employing, as a template, genomic DNA extracted from the transformant, and two primer sets (amyEfw2 and secE/Ne-R, and secE/Y-F2 and amyErv2) shown in Table 1 indicated that 2.6 kb and 2.4 kb DNA fragments were amplified, and that the DNA fragment in which the secY gene was ligated to the downstream of the transcription initiation regulatory region and ribosome-binding site of the spoVG gene, and the secE gene was ligated to the downstream of the secY gene was inserted into the amyE gene site in the genome of *Bacillus subtilis* 168 strain. Since no transcription termination site is present between the secY gene and the secE gene, the secE gene is considered to be transcribed, as the same transcription unit as the secY gene, by the action of the transcription initiation regulatory region of the spoVG gene. The thus-obtained strain was denominated "secYE-K strain." Meanwhile, in a manner similar to that in Example 1, secG-K strain was constructed, in which a DNA fragment in which the secG gene was ligated to the downstream of the transcription initiation regulatory region and ribosome-binding site of the spoVG gene was inserted into the amyE gene site in the genome of *Bacillus subtilis* 168 strain. The secG-K strain was constructed by use of primers shown in Table 1. Table 3 shows the primers employed for constructing the secG-K strain and the secY-K strain.

TABLE 3

|  | For construction of secY-K strain | For construction of secG-K strain |
|---|---|---|
| Amplification of fragment (A) | PVG-FW<br>PVG-R | PVG-FW<br>PVG-R |
| Amplification of fragment (B) | secY/PVG-F<br>secY/Cm-R | secG/PVGf<br>secG/Ne-R |
| Amplification of fragment (C) | catf<br>catr | rneof<br>Nmr |
| Amplification of fragment (D) | PVG-FW2<br>catr2 | PVG-FW2<br>Nmr |
| Amplification of fragment (E) | amyEfw2<br>amyE/PVG2-R | amyEfw2<br>amyE/PVG2-R |
| Amplification of fragment (F) | amyE/Cm2-F<br>amyErv2 | amyE/Nm-F<br>amyErv2 |
| Amplification of fragment (G) | amyEfw1<br>amyErv1 | amyEfw1<br>amyErv1 |

Comparative Example 2

Evaluation of Secretion/Production of Alkaline Cellulase

Alkaline cellulase productivities of the strains constructed in Comparative Example 1 were evaluated in a manner similar to that in Example 2. For comparison, *Bacillus subtilis* 168 strain (control) and the secY-K strain constructed in Example 1 were also evaluated in terms of alkaline cellulase productivity.

As shown in Table 4, the secG-K strain, which overexpressed the secG gene, exhibited cellulase productivity slightly higher than that of the 168 strain (wild-type strain) but lower than that of the secY-K strain. The secYE-K strain, which overexpressed both the secY gene and the secE gene, exhibited cellulase productivity comparable to that of the secY-K strain; i.e., the effect of overexpression of the secE gene was not observed. As is clear from these data, among the three Sec proteins (SecY, SecE, and SecG) constituting a main portion of the transport channel of secretory protein, an increase in amount of SecY protein is highly effective for enhancement of secretion efficiency of cellulase.

TABLE 4

| Strain name | Overexpressed gene | Amount of secreted/produced alkaline cellulase (relative value) |
|---|---|---|
| secG-K strain | secG | 108 |
| secYE-K strain | secY and secE | 115 |
| secY-K strain | secY | 117 |
| 168 strain | None | 100 |

Comparative Example 3

Evaluation of Secretion/Production of Alkaline Amylase

Alkaline amylase productivities of the secY-K strain constructed in Example 1 and the secG-K strain constructed in Comparative Example 1 were evaluated as follows. Specifically, a 1.5 kb DNA fragment encoding alkaline amylase (Appl. Environ. Microbiol., 67, 1744, (2001)) was amplified through PCR by using, as a template, genomic DNA extract from *Bacillus* sp. KSM-K38 strain (FERM BP-6946), and a primer set (K38matu-F2 (ALAA) and SP64K38-R (XbaI)). Also, a 0.6 kb DNA fragment including the promoter region and secretion-signal-sequence-encoding region of an alkaline cellulase gene (JP-A-2000-210081) was amplified through PCR by using, as a template, genomic DNA extracted from *Bacillus* sp. KSM-S237 strain (FERM BP-7875), and a primer set (S237 ppp-F2 (BamHI) and S237 ppp-R2 (ALAA)). Subsequently, SOE-PCR was carried out by use of the thus-prepared two fragments in combination as templates, and by use of a primer set (S237 ppp-F2 (BamHI) and SP64K38-R (XbaI)), to thereby yield a 2.1 kb DNA fragment in which the alkaline amylase gene was ligated to the downstream of the promoter region and secretion-signal-sequence-encoding region of the alkaline cellulase gene. The thus-obtained 2.1 kb DNA fragment was inserted into the restriction enzyme BamHI-XbaI cleavage site of a shuttle vector pHY300PLK (product of Yakult), to thereby construct a plasmid pHYK38(S237 ps) for evaluation of alkaline amylase productivity.

The thus-constructed plasmid pHYK38(S237 ps) was introduced into the secY-K strain, the secG-K strain, or *Bacillus subtilis* 168 strain (control) through the protoplast transformation method. Cells of the thus-obtained recombinant strain were shake-cultured for five days under conditions similar to those described above in Example 2. After completion of culturing, cells were removed through centrifugation, and alkaline amylase activity of the culture supernatant was determined, to thereby calculate the amount of amylase extracellularly secreted from the cells during culturing. Amylase activity of the culture supernatant was determined by means of Liquitec Amy EPS (product of Roche Diagnostic). Specifically, an R1-R2 mixture (100 μL) (R1 (coupling enzyme): R2 (amylase substrate)=5:1 (vol.)) was added to and mixed with a sample solution (50 μL) appropriately diluted with 1% NaCl-1/7.5 M phosphate buffer (pH 7.4, product of Wako Pure Chemical Industries, Ltd.), and the amount of p-nitrophenol released during reaction at 30° C. was quantitatively determined on the basis of a change in absorbance at 405 nm (OD 405 nm). The amount of enzyme required for release of 1 μmol of p-nitrophenol for one minute was defined as 1 U.

TABLE 5

| Strain name | Overexpressed gene | Amount of secreted/produced alkaline amylase (relative value) |
|---|---|---|
| secG-K strain | secG | 94 |
| secY-K strain | secY | 61 |
| 168 strain | None | 100 |

As is clear from Table 5, the secG-K strain, which overexpressed the secG gene, exhibited amylase productivity slightly lower than that of the 168 strain (wild-type strain), and the secY-K strain exhibited amylase productivity considerably lower than that of the wild-type strain; i.e., an increase in amount of SecY protein adversely affected amylase productivity. These data suggest that overexpression of the secY gene contributes especially to enhancement of cellulase productivity.

The gene numbers and functions of genes in relation to the present invention are shown in Table 6.

TABLE 6

| Gene name | Gene number | Function |
|---|---|---|
| secY | BG10445 | Preprotein translocase SecY subunit |
| spoVG | BG10112 | Sporulation stage V protein G (spore cortex synthesis) |
| amyE | BG10473 | α-amylase |
| secG | BG14067 | Preprotein translocase SecG subunit |
| secE | BG10161 | Preprotein translocase SecE subunit |
| rpsJ | BG19008 | 30S ribosomal protein S10 |
| ybxG | BG11505 | Putative amino acid transporter |
| aprE | BG10190 | Alkaline serine protease |
| sacB | BG10388 | Levansucrase |
| nprE | BG10448 | Extracellular neutral metal protease |

The names, numbers, functions, etc. of these genes conform with the *Bacillus subtilis* genome data reported by Kunst, et al. (Nature, 390, 249-256, 1997) and made public by JAPAN (Japan Functional Analysis Network for *Bacillus subtilis*; BSORF DB) on the Internet (*bacillus*.genome.ad.jp, renewed Mar. 10, 2004).

Comparative Example 4

Construction of Another-Sec-Gene-Overexpressing Strain-2

A strain overexpressing both the secY gene and the secG gene was constructed in a manner similar to that in Comparative Example 1. Specifically, among the primers employed for constructing the secYE-K strain, secE/Y-F2 and secE/Ne-R were respectively substituted with secG/Y-F2 and secG/Ne-R shown in Table 7, to thereby construct secYG-K strain.

In a manner similar to that in Example 1, secE-K strain was constructed, in which a DNA fragment in which the secE gene was ligated to the downstream of the transcription initiation regulatory region and ribosome-binding site of the spoVG gene was inserted into the amyE gene site in the genome of *Bacillus subtilis* 168 strain. For construction of the secE-K strain, among the primers employed for the secY-K strain, secY/PVG-F and secY/Cm-R were respectively substituted with secE/PVG-F and secE/Cm-R shown in Table 7.

Alkaline cellulase productivities of the above-constructed strains were evaluated in a manner similar to that in Example 2. For comparison, *Bacillus subtilis* 168 strain (control) and the secY-K strain constructed in Example 1 were also evaluated in terms of alkaline cellulase productivity.

TABLE 7

| Primer | Sequence (5'-3') | SEQ ID NO |
|---|---|---|
| secG/Y-F2 | GTGGATTTATGAAAAACTAGTGAGTCTGGAGGTGTATGGG | 38 |
| secG/Ne-R | TATTTTATAAACTCATTCCCCCCTATAGGATATAAGCAAG | 39 |
| secE/PVG-F | GGAAAAGGTGGTGAACTACTATGCGTATTATGAAATTCTTTAAAGATG | 40 |
| secE/Cm-R | ATGGGTGCTTTAGTTGAAGATTATTCAACTATTAAACGAATTAATTGA | 41 |

As shown in Table 8, the secYG-K strain, which overexpressed both the secY gene and the secG gene, exhibited cellulase productivity comparable to that of the secY-K strain; i.e., the effect of overexpression of the secG gene was not observed. As shown in Table 9, the secE-K strain, which overexpressed the secE gene, exhibited cellulase productivity slightly higher than that of the 168 strain (wild-type strain) but lower than that of the secY-K strain. As is clear from these data, among the three Sec proteins (SecY, SecE, and SecG) constituting a main portion of the transport channel of secretory protein, an increase in amount of SecY protein is highly effective for enhancement of secretion efficiency of cellulase.

TABLE 8

| Strain name | Overexpressed gene | Amount of secreted/produced alkaline cellulase (relative value) |
|---|---|---|
| secYG-K strain | secY and secG | 118 |
| secY-K strain | secY | 118 |
| 168 strain | None | 100 |

TABLE 9

| Strain name | Overexpressed gene | Amount of secreted/produced alkaline cellulase (relative value) |
|---|---|---|
| secE-K strain | secE | 105 |
| secY-K strain | secY | 113 |
| 168 strain | None | 100 |

Comparative Example 5

Evaluation of Secretion/Production of Alkaline Protease

Alkaline protease productivity of the secY-K strain constructed in Example 1 was evaluated as described below. For comparison, *Bacillus subtilis* 168 strain (control) was also evaluated in terms of alkaline protease productivity. Specifically, a 1.3 kb DNA fragment encoding alkaline protease (Appl. Microbiol. Biotechnol., 43, 473, (1995)) having the amino acid sequence represented by SEQ ID NO: 42 was amplified through PCR by using, as a template, genomic DNA extracted from *Bacillus clausii* KSM-K16 strain (FERM BP-3376), and a primer set (S237pKAPpp-F and KAPter-R (BglII)) shown in Table 10. Also, a 0.6 kb DNA fragment including the promoter region of an alkaline cellulase gene (JP-A-2000-210081) was amplified through PCR by using, as a template, genomic DNA extracted from *Bacillus* sp. KSM-S237 strain (FERM BP-7875), and a primer set (S237 ppp-F2 (BamHI) and S237pKAPpp-R) shown in Table 10. Subsequently, SOE-PCR was carried out by use of the thus-obtained two fragments in combination as templates, and by use of a primer set (S237 ppp-F2 (BamHI) and KAPter-R (BglII)) shown in Table 10, to thereby yield a 1.8 kb DNA fragment in which the alkaline protease gene was ligated to the downstream of the promoter region of the alkaline cellulase gene. The thus-obtained 1.8 kb DNA fragment was inserted into the restriction enzyme BamHI-BglII cleavage site of a shuttle vector pHY300PLK (product of Yakult), to thereby construct a plasmid pHYKAP(S237p) for evaluation of alkaline protease productivity.

The thus-constructed plasmid pHYKAP(S237p) was introduced into the secY-K strain or *Bacillus subtilis* 168 strain (control) through the protoplast transformation method. Cells of the thus-obtained recombinant strain were shake-cultured in an LB medium (10 mL) overnight at 37° C. The resultant culture liquid (0.05 mL) was inoculated into a 2×L-maltose medium (50 mL) (2% tryptone, 1% yeast extract, 1% NaCl, 7.5% maltose, 7.5 ppm manganese sulfate 4-5 hydrate, and 15 ppm tetracycline), followed by shake culturing at 30° C. for three days. After completion of culturing, cells were removed through centrifugation, and alkaline protease activity of the culture supernatant was determined, to thereby calculate the amount of alkaline protease extracellularly secreted from the cells during culturing. Protease activity of the culture supernatant was determined as follows. Specifically, 75 mM borate-KCl buffer (pH 10.5) (100 μL) containing 7.5 mM succinyl-L-alanyl-L-alanyl-L-alanine p-nitroanilide (STANA; product of Peptide Institute Inc.) as a substrate was added to and mixed with the culture supernatant (50 μL) appropriately diluted with a 2 mM calcium chloride solution, and the amount of p-nitroaniline released during reaction at 30° C. was quantitatively determined on the basis of a change in absorbance at 420 nm (OD 420 nm). The amount of enzyme required for release of 1 μmol of p-nitroaniline for one minute was defined as 1 U.

TABLE 10

| Primer | Sequence (5'-3') | SEQ ID NO |
|---|---|---|
| S237pKAPpp-F | ACTTTAAAAATATTTAGGAGGTAATATGAAGAAACCGTTGGGGAAA | 44 |
| KAPter-R (BglII) | GGGAGATCTTCAGCGATCTATTTCTCTTTTTC | 45 |
| S237ppp-F2 (BamHI) | CCCGGATCCAACAGGCTTATATTTA | 46 |
| S237pKAPpp-R | TTTCCCCAACGGTTTCTTCATATTACCTCCTAAATATTTTTAAAGT | 47 |

As is clear from Table 11, when the secY-K strain was employed as a host, alkaline protease productivity was comparable to that in the case where the control 168 strain (wild-type strain) was employed, and no particular enhancement of alkaline protease productivity was observed; i.e., an increase in amount of SecY protein did not affect protease productivity. These data, together with the data obtained in Comparative Example 3, suggest that overexpression of the secY gene contributes specifically to enhancement of cellulase productivity.

TABLE 11

| Strain name | Overexpressed gene | Amount of secreted/produced protease (relative value) |
|---|---|---|
| secY-K strain | secY | 100 |
| 168 strain | None | 100 |

The invention claimed is:

1. A recombinant *Bacillus* microorganism comprising a gene encoding cellulase,
wherein said *Bacillus* microorganism is modified to overexpress a *Bacillus* secY gene, or *Bacillus* secY and secE genes as compared to the corresponding *Bacillus* microorganism lacking said modification, and
wherein said recombinant *Bacillus* microorganism has not been modified to alter the endogenous expression of secG.

2. The recombinant *Bacillus* microorganism of claim 1, wherein:
i) a transcription initiation regulatory region or both the transcription initiation regulatory region and a ribosome-binding site, which function in the recombinant *Bacillus* microorganism, is introduced upstream of the *Bacillus* secY gene;
ii) a transcription initiation regulatory region or both the transcription initiation regulatory region and a ribosome-binding site, which function in the recombinant *Bacillus* microorganism, is introduced upstream of the leading gene of an operon including the *Bacillus* secY gene; or
iii) a gene fragment prepared by ligating a transcription initiation regulatory region or both the transcription initiation regulatory region and a ribosome-binding site to the upstream of the *Bacillus* secY gene is introduced.

3. The recombinant *Bacillus* microorganism of claim 2, wherein the transcription initiation regulatory region or both the transcription initiation regulatory region and the ribosome-binding site are those of a *Bacillus* spoVG gene or a *Bacillus* aprE gene.

4. The recombinant *Bacillus* microorganism of claim 1, wherein said recombinant *Bacillus* microorganism is *Bacillus subtilis*.

5. The recombinant *Bacillus* microorganism of any one of claims 1 to 3, wherein one or more regions selected from the group consisting of a transcription initiation regulatory region, a translation initiation regulatory region, and a secretion signal region are ligated upstream of the gene encoding cellulase.

6. The recombinant *Bacillus* microorganism of claim 5, wherein the transcription initiation regulatory region; the translation initiation regulatory region; and the secretion signal region, are ligated to the upstream of the gene encoding cellulase.

7. The recombinant *Bacillus* microorganism of claim 5, wherein the secretion signal region is derived from a cellulose gene of a bacterium belonging to the genus *Bacillus*, and the transcription initiation regulatory region and the translation initiation regulatory region are derived from a 0.6 to 1 kb region upstream of the cellulase gene.

8. The recombinant *Bacillus* microorganism of claim 6, wherein the transcription initiation regulatory region, the translation initiation regulatory region, and the secretion signal region are a DNA fragment selected from the group consisting of: i) a DNA fragment having a nucleotide sequence represented by nucleotide numbers 1 to 659 of a cellulase gene consisting of a nucleotide sequence represented by SEQ ID NO:3; ii) a DNA fragment having a nucleotide sequence represented by nucleotide numbers 1 to 696 of a cellulase gene consisting of a nucleotide sequence represented by SEQ ID NO:5; iii) a DNA fragment having a nucleotide sequence that is at least 70% identical, to nucleotides 1-659 of SEQ ID NO:3, or that is at least 70% identical to nucleotides 1 to 696 of SEQ ID NO:5; and iv) a DNA fragment having a nucleotide sequence obtained through partial deletion of the DNA fragment of i), ii), or iii).

9. The recombinant *Bacillus* microorganism of claim 1, wherein said *Bacillus* secY gene is a *Bacillus subtilis* secY gene.

10. The recombinant *Bacillus* microorganism of claim 1, wherein said recombinant *Bacillus microorganism* is *Bacillus subtilis* and said *Bacillus* secY gene is a *Bacillus subtilis* secY gene.

11. The recombinant *Bacillus* microorganism of claim 1, wherein said *Bacillus* secE gene is a *Bacillus subtilis* secE gene.

12. The recombinant *Bacillus* microorganism of claim 1, wherein said recombinant *Bacillus* microorganism is *Bacillus subtilis* and said *Bacillus* secE gene is a *Bacillus subtilis* secE gene.

13. A method for producing cellulase, comprising:

i. culturing the recombinant *Bacillus* microorganism of any one of claims 1 to 3 in a culture medium under conditions that permit the expression of the cellulase gene; and ii. collecting the cellulase protein from the culture medium.

* * * * *

SEQUENCE LISTING

<160> NUMBER OF SEQ ID NOS: 47

<210> SEQ ID NO 1
<211> LENGTH: 1296
<212> TYPE: DNA
<213> ORGANISM: Bacillus subtilis
<220> FEATURE:
<221> NAME/KEY: CDS
<222> LOCATION: (1)..(1296)

<400> SEQUENCE: 1

```
ttg ttt aaa aca atc tcc aac ttt atg cgt gtg agt gat atc agg aat       48
Leu Phe Lys Thr Ile Ser Asn Phe Met Arg Val Ser Asp Ile Arg Asn
1               5                   10                  15 aaa atc ata ttc act tta ctc atg ctt atc gtc ttt cgc ata ggt gcg       96
Lys Ile Ile Phe Thr Leu Leu Met Leu Ile Val Phe Arg Ile Gly Ala
            20                  25                  30 ttt att cct gtg cct tac gtt aac gct gaa gcg tta cag gca cag tct      144
Phe Ile Pro Val Pro Tyr Val Asn Ala Glu Ala Leu Gln Ala Gln Ser
        35                  40                  45 caa atg ggt gtt ttt gat ctc ctt aat aca ttt ggc ggc ggt gcg ctt      192
Gln Met Gly Val Phe Asp Leu Leu Asn Thr Phe Gly Gly Gly Ala Leu
    50                  55                  60 tac caa ttt tcc att ttc gca atg gga att act cct tat atc acg gct      240
Tyr Gln Phe Ser Ile Phe Ala Met Gly Ile Thr Pro Tyr Ile Thr Ala
65                  70                  75                  80 tcg atc atc att cag ctg ctt cag atg gat gtg gta ccg aag ttt acc      288
Ser Ile Ile Ile Gln Leu Leu Gln Met Asp Val Val Pro Lys Phe Thr
                85                  90                  95 gag tgg tct aag caa ggt gaa gtt ggc cgc cgt aaa tta gct cag ttc      336
Glu Trp Ser Lys Gln Gly Glu Val Gly Arg Arg Lys Leu Ala Gln Phe
            100                 105                 110 aca agg tac ttt acg att gtg ctt ggt ttc atc caa gcg tta ggt atg      384
Thr Arg Tyr Phe Thr Ile Val Leu Gly Phe Ile Gln Ala Leu Gly Met
        115                 120                 125 tca tat gga ttc aac aat ctg gca aac ggt atg ctg atc gaa aaa tcc      432
Ser Tyr Gly Phe Asn Asn Leu Ala Asn Gly Met Leu Ile Glu Lys Ser
    130                 135                 140 ggt gta tcg aca tat ctt atc att gct tta gtg ctc act ggc gga act      480
Gly Val Ser Thr Tyr Leu Ile Ile Ala Leu Val Leu Thr Gly Gly Thr
145                 150                 155                 160 gcc ttt tta atg tgg ctt ggg gaa caa att act tct cat gga gta ggc      528
Ala Phe Leu Met Trp Leu Gly Glu Gln Ile Thr Ser His Gly Val Gly
                165                 170                 175 aac gga ata tcg atc att atc ttc gcg ggg att gtg tct agt att cca      576
Asn Gly Ile Ser Ile Ile Ile Phe Ala Gly Ile Val Ser Ser Ile Pro
            180                 185                 190 aaa aca att ggg caa ata tat gag act caa ttt gtc ggc agc aac gat      624
Lys Thr Ile Gly Gln Ile Tyr Glu Thr Gln Phe Val Gly Ser Asn Asp
        195                 200                 205 cag ttg ttt att cat att gtg aaa gtc gca ctt ctt gtg att gcg att      672
Gln Leu Phe Ile His Ile Val Lys Val Ala Leu Leu Val Ile Ala Ile
    210                 215                 220 tta gca gtt att gtt gga gtt att ttc att cag caa gcc gta cgg aaa      720
Leu Ala Val Ile Val Gly Val Ile Phe Ile Gln Gln Ala Val Arg Lys
225                 230                 235                 240 att gcg att caa tat gct aaa ggc aca ggt cgt tca cct gct ggc gga      768
Ile Ala Ile Gln Tyr Ala Lys Gly Thr Gly Arg Ser Pro Ala Gly Gly
                245                 250                 255 ggt cag tct aca cac ctt cca ttg aaa gtg aat cct gca ggg gtt att      816
```

```
ccg gta atc ttt gcg gtt gcg ttt ttg ata acg ccg cgg acg atc gcg    864
Pro Val Ile Phe Ala Val Ala Phe Leu Ile Thr Pro Arg Thr Ile Ala
    275                 280                 285 tca ttc ttt gga aca aac gat gtg aca aag tgg att caa aac aac ttt    912
Ser Phe Phe Gly Thr Asn Asp Val Thr Lys Trp Ile Gln Asn Asn Phe
    290                 295                 300 gat aat acg cat ccg gtg ggt atg gcg ata tat gtt gcg ttg att att    960
Asp Asn Thr His Pro Val Gly Met Ala Ile Tyr Val Ala Leu Ile Ile
305                 310                 315                 320 gcc ttt acg tac ttt tat gct ttt gta cag gta aac cct gaa caa atg   1008
Ala Phe Thr Tyr Phe Tyr Ala Phe Val Gln Val Asn Pro Glu Gln Met
                325                 330                 335 gct gat aac ctt aaa aaa cag ggt ggc tat atc ccg ggg gtt cgt cca   1056
Ala Asp Asn Leu Lys Lys Gln Gly Gly Tyr Ile Pro Gly Val Arg Pro
                340                 345                 350 ggg aaa atg act caa gat aga att acg agc att ttg tat cga ctt acg   1104
Gly Lys Met Thr Gln Asp Arg Ile Thr Ser Ile Leu Tyr Arg Leu Thr
            355                 360                 365 ttt gtg ggt tct ata ttc tta gcc gtg att tcc att ctt cct atc ttt   1152
Phe Val Gly Ser Ile Phe Leu Ala Val Ile Ser Ile Leu Pro Ile Phe
370                 375                 380 ttc att caa ttc gct gga ttg cct caa agt gca caa att ggc gga aca   1200
Phe Ile Gln Phe Ala Gly Leu Pro Gln Ser Ala Gln Ile Gly Gly Thr
385                 390                 395                 400 tct ttg tta att gtt gtc ggg gta gcc ttg gag aca atg aaa caa cta   1248
Ser Leu Leu Ile Val Val Gly Val Ala Leu Glu Thr Met Lys Gln Leu
                405                 410                 415 gaa agc cag ttg gtg aaa cga aac tac cgt gga ttt atg aaa aac tag   1296
Glu Ser Gln Leu Val Lys Arg Asn Tyr Arg Gly Phe Met Lys Asn
                420                 425                 430

<210> SEQ ID NO 2
<211> LENGTH: 431
<212> TYPE: PRT
<213> ORGANISM: Bacillus subtilis

<400> SEQUENCE: 2

Leu Phe Lys Thr Ile Ser Asn Phe Met Arg Val Ser Asp Ile Arg Asn
1               5                   10                  15

Lys Ile Ile Phe Thr Leu Leu Met Leu Ile Val Phe Arg Ile Gly Ala
            20                  25                  30

Phe Ile Pro Val Pro Tyr Val Asn Ala Glu Ala Leu Gln Ala Gln Ser
        35                  40                  45

Gln Met Gly Val Phe Asp Leu Leu Asn Thr Phe Gly Gly Gly Ala Leu
    50                  55                  60

Tyr Gln Phe Ser Ile Phe Ala Met Gly Ile Thr Pro Tyr Ile Thr Ala
65                  70                  75                  80

Ser Ile Ile Ile Gln Leu Leu Gln Met Asp Val Val Pro Lys Phe Thr
                85                  90                  95

Glu Trp Ser Lys Gln Gly Glu Val Gly Arg Arg Lys Leu Ala Gln Phe
            100                 105                 110

Thr Arg Tyr Phe Thr Ile Val Leu Gly Phe Ile Gln Ala Leu Gly Met
        115                 120                 125

Ser Tyr Gly Phe Asn Asn Leu Ala Asn Gly Met Leu Ile Glu Lys Ser
    130                 135                 140

Gly Val Ser Thr Tyr Leu Ile Ile Ala Leu Val Leu Thr Gly Gly Thr
145                 150                 155                 160
```

```
Ala Phe Leu Met Trp Leu Gly Glu Gln Ile Thr Ser His Gly Val Gly
            165                 170                 175

Asn Gly Ile Ser Ile Ile Ile Phe Ala Gly Ile Val Ser Ser Ile Pro
            180                 185                 190

Lys Thr Ile Gly Gln Ile Tyr Glu Thr Gln Phe Val Gly Ser Asn Asp
            195                 200                 205

Gln Leu Phe Ile His Ile Lys Val Ala Leu Leu Val Ile Ala Ile
        210                 215                 220

Leu Ala Val Ile Val Gly Val Phe Ile Gln Gln Ala Val Arg Lys
225                 230                 235                 240

Ile Ala Ile Gln Tyr Ala Lys Gly Thr Gly Arg Ser Pro Ala Gly Gly
            245                 250                 255

Gly Gln Ser Thr His Leu Pro Leu Lys Val Asn Pro Ala Gly Val Ile
            260                 265                 270

Pro Val Ile Phe Ala Val Ala Phe Leu Ile Thr Pro Arg Thr Ile Ala
            275                 280                 285

Ser Phe Phe Gly Thr Asn Asp Val Thr Lys Trp Ile Gln Asn Asn Phe
            290                 295                 300

Asp Asn Thr His Pro Val Gly Met Ala Ile Tyr Val Ala Leu Ile Ile
305                 310                 315                 320

Ala Phe Thr Tyr Phe Tyr Ala Phe Val Gln Val Asn Pro Glu Gln Met
            325                 330                 335

Ala Asp Asn Leu Lys Lys Gln Gly Gly Tyr Ile Pro Gly Val Arg Pro
            340                 345                 350

Gly Lys Met Thr Gln Asp Arg Ile Thr Ser Ile Leu Tyr Arg Leu Thr
            355                 360                 365

Phe Val Gly Ser Ile Phe Leu Ala Val Ile Ser Ile Leu Pro Ile Phe
            370                 375                 380

Phe Ile Gln Phe Ala Gly Leu Pro Gln Ser Ala Gln Ile Gly Gly Thr
385                 390                 395                 400

Ser Leu Leu Ile Val Val Gly Val Ala Leu Glu Thr Met Lys Gln Leu
            405                 410                 415

Glu Ser Gln Leu Val Lys Arg Asn Tyr Arg Gly Phe Met Lys Asn
            420                 425                 430

<210> SEQ ID NO 3
<211> LENGTH: 3150
<212> TYPE: DNA
<213> ORGANISM: Bacillus sp. KSM-S237
<220> FEATURE:
<221> NAME/KEY: CDS
<222> LOCATION: (573)..(3044)
<220> FEATURE:
<221> NAME/KEY: sig_peptide
<222> LOCATION: (573)..(659)
<220> FEATURE:
<221> NAME/KEY: mat_peptide
<222> LOCATION: (660)..(3044)

<400> SEQUENCE: 3
gatttgccga tgcaacaggc ttatatttag aggaaatttc ttttaaatt gaatacggaa      60 taaaatcagg taaacaggtc ctgattttat ttttttgagt tttttagaga actgaagatt    120
gaaataaaag tagaagacaa aggacataag aaaattgcat tagttttaat tatagaaaac    180 gccttttat aattatttat acctagaacg aaaatactgt ttcgaaagcg gtttactata     240
aaaccttata ttccggctct tttttaaaac agggggtaaa aattcactct agtattctaa    300
tttcaacatg ctataataaa tttgtaagac gcaatatgca tctcttttt tacgatatat     360
```

```
gtaagcggtt aaccttgtgc tatatgccga tttaggaagg ggggtagatt gagtcaagta      420
gtaataatat agataactta taagttgttg agaagcagga gagcatctgg gttactcaca      480
agttttttta aaactttaac gaaagcactt tcggtaatgc ttatgaattt agctatttga      540
ttcaattact ttaaaaatat ttaggaggta at atg atg tta aga aag aaa aca       593
                                   Met Met Leu Arg Lys Lys Thr
                                                      -25 aag cag ttg att tct tcc att ctt att tta gtt tta ctt cta tct tta       641
Lys Gln Leu Ile Ser Ser Ile Leu Ile Leu Val Leu Leu Leu Ser Leu
        -20                 -15                 -10 ttt ccg gca gct ctt gca gca gaa gga aac act cgt gaa gac aat ttt       689
Phe Pro Ala Ala Leu Ala Ala Glu Gly Asn Thr Arg Glu Asp Asn Phe
 -5              -1   1               5                      10 aaa cat tta tta ggt aat gac aat gtt aaa cgc cct tct gag gct ggc       737
Lys His Leu Leu Gly Asn Asp Asn Val Lys Arg Pro Ser Glu Ala Gly
                 15                  20                  25 gca tta caa tta caa gaa gtc gat gga caa atg aca tta gta gat caa       785
Ala Leu Gln Leu Gln Glu Val Asp Gly Gln Met Thr Leu Val Asp Gln
             30                  35                  40 cat gga gaa aaa att caa tta cgt gga atg agt aca cac gga tta cag       833
His Gly Glu Lys Ile Gln Leu Arg Gly Met Ser Thr His Gly Leu Gln
         45                  50                  55 tgg ttt cct gag atc ttg aat gat aac gca tac aaa gct ctt tct aac       881
Trp Phe Pro Glu Ile Leu Asn Asp Asn Ala Tyr Lys Ala Leu Ser Asn
     60                  65                  70 gat tgg gat tcc aat atg att cgt ctt gct atg tat gta ggt gaa aat       929
Asp Trp Asp Ser Asn Met Ile Arg Leu Ala Met Tyr Val Gly Glu Asn
 75                  80                  85                  90 ggg tac gct aca aac cct gag tta atc aaa caa aga gtg att gat gga       977
Gly Tyr Ala Thr Asn Pro Glu Leu Ile Lys Gln Arg Val Ile Asp Gly
                 95                 100                 105 att gag tta gcg att gaa aat gac atg tat gtt att gtt gac tgg cat      1025
Ile Glu Leu Ala Ile Glu Asn Asp Met Tyr Val Ile Val Asp Trp His
             110                 115                 120 gtt cat gcg cca ggt gat cct aga gat cct gtt tat gca ggt gct aaa      1073
Val His Ala Pro Gly Asp Pro Arg Asp Pro Val Tyr Ala Gly Ala Lys
         125                 130                 135 gat ttc ttt aga gaa att gca gct tta tac cct aat aat cca cac att      1121
Asp Phe Phe Arg Glu Ile Ala Ala Leu Tyr Pro Asn Asn Pro His Ile
     140                 145                 150 att tat gag tta gcg aat gag ccg agt agt aat aat aat ggt gga gca      1169
Ile Tyr Glu Leu Ala Asn Glu Pro Ser Ser Asn Asn Asn Gly Gly Ala
155                 160                 165                 170 ggg att ccg aat aac gaa gaa ggt tgg aaa gcg gta aaa gaa tat gct      1217
Gly Ile Pro Asn Asn Glu Glu Gly Trp Lys Ala Val Lys Glu Tyr Ala
                 175                 180                 185 gat cca att gta gaa atg tta cgt aaa agc ggt aat gca gat gac aac      1265
Asp Pro Ile Val Glu Met Leu Arg Lys Ser Gly Asn Ala Asp Asp Asn
             190                 195                 200 att atc att gtt ggt agt cca aac tgg agt cag cgt ccg gac tta gca      1313
Ile Ile Ile Val Gly Ser Pro Asn Trp Ser Gln Arg Pro Asp Leu Ala
         205                 210                 215 gct gat aat cca att gat gat cac cat aca atg tat act gtt cac ttc      1361
Ala Asp Asn Pro Ile Asp Asp His His Thr Met Tyr Thr Val His Phe
     220                 225                 230 tac act ggt tca cat gct gct tca act gaa agc tat ccg tct gaa act      1409
Tyr Thr Gly Ser His Ala Ala Ser Thr Glu Ser Tyr Pro Ser Glu Thr
235                 240                 245                 250 cct aac tct gaa aga gga aac gta atg agt aac act cgt tat gcg tta      1457
```

```
Pro Asn Ser Glu Arg Gly Asn Val Met Ser Asn Thr Arg Tyr Ala Leu
            255                 260                 265 gaa aac gga gta gcg gta ttt gca aca gag tgg gga acg agt caa gct      1505
Glu Asn Gly Val Ala Val Phe Ala Thr Glu Trp Gly Thr Ser Gln Ala
            270                 275                 280 agt gga gac ggt ggt cct tac ttt gat gaa gca gat gta tgg att gaa      1553
Ser Gly Asp Gly Gly Pro Tyr Phe Asp Glu Ala Asp Val Trp Ile Glu
            285                 290                 295 ttt tta aat gaa aac aac att agc tgg gct aac tgg tct tta acg aat      1601
Phe Leu Asn Glu Asn Asn Ile Ser Trp Ala Asn Trp Ser Leu Thr Asn
        300                 305                 310 aaa aat gaa gta tct ggt gca ttt aca cca ttc gag tta ggt aag tct      1649
Lys Asn Glu Val Ser Gly Ala Phe Thr Pro Phe Glu Leu Gly Lys Ser
315                 320                 325                 330 aac gca acc aat ctt gac cca ggt cca gat cat gtg tgg gca cca gaa      1697
Asn Ala Thr Asn Leu Asp Pro Gly Pro Asp His Val Trp Ala Pro Glu
                335                 340                 345 gaa tta agt ctt tct gga gaa tat gta cgt gct cgt att aaa ggt gtg      1745
Glu Leu Ser Leu Ser Gly Glu Tyr Val Arg Ala Arg Ile Lys Gly Val
            350                 355                 360 aac tat gag cca atc gac cgt aca aaa tac acg aaa gta ctt tgg gac      1793
Asn Tyr Glu Pro Ile Asp Arg Thr Lys Tyr Thr Lys Val Leu Trp Asp
            365                 370                 375 ttt aat gat gga acg aag caa gga ttt gga gtg aat tcg gat tct cca      1841
Phe Asn Asp Gly Thr Lys Gln Gly Phe Gly Val Asn Ser Asp Ser Pro
        380                 385                 390 aat aaa gaa ctt att gca gtt gat aat gaa aac aac act ttg aaa gtt      1889
Asn Lys Glu Leu Ile Ala Val Asp Asn Glu Asn Asn Thr Leu Lys Val
395                 400                 405                 410 tcg gga tta gat gta agt aac gat gtt tca gat ggc aac ttc tgg gct      1937
Ser Gly Leu Asp Val Ser Asn Asp Val Ser Asp Gly Asn Phe Trp Ala
                415                 420                 425 aat gct cgt ctt tct gcc aac ggt tgg gga aaa agt gtt gat att tta      1985
Asn Ala Arg Leu Ser Ala Asn Gly Trp Gly Lys Ser Val Asp Ile Leu
            430                 435                 440 ggt gct gag aag ctt aca atg gat gtt att gtt gat gaa cca acg acg      2033
Gly Ala Glu Lys Leu Thr Met Asp Val Ile Val Asp Glu Pro Thr Thr
            445                 450                 455 gta gct att gcg gcg att cca caa agt agt aaa agt gga tgg gca aat      2081
Val Ala Ile Ala Ala Ile Pro Gln Ser Ser Lys Ser Gly Trp Ala Asn
        460                 465                 470 cca gag cgt gct gtt cga gtg aac gcg gaa gat ttt gtc cag caa acg      2129
Pro Glu Arg Ala Val Arg Val Asn Ala Glu Asp Phe Val Gln Gln Thr
475                 480                 485                 490 gac ggt aag tat aaa gct gga tta aca att aca gga gaa gat gct cct      2177
Asp Gly Lys Tyr Lys Ala Gly Leu Thr Ile Thr Gly Glu Asp Ala Pro
                495                 500                 505 aac cta aaa aat atc gct ttt cat gaa gaa gat aac aat atg aac aac      2225
Asn Leu Lys Asn Ile Ala Phe His Glu Glu Asp Asn Asn Met Asn Asn
            510                 515                 520 atc att ctg ttc gtg gga act gat gca gct gac gtt att tac tta gat      2273
Ile Ile Leu Phe Val Gly Thr Asp Ala Ala Asp Val Ile Tyr Leu Asp
            525                 530                 535 aac att aaa gta att gga aca gaa gtt gaa att cca gtt gtt cat gat      2321
Asn Ile Lys Val Ile Gly Thr Glu Val Glu Ile Pro Val Val His Asp
        540                 545                 550 cca aaa gga gaa gct gtt ctt cct tct gtt ttt gaa gac ggt aca cgt      2369
Pro Lys Gly Glu Ala Val Leu Pro Ser Val Phe Glu Asp Gly Thr Arg
555                 560                 565                 570 caa ggt tgg gac tgg gct gga gag tct ggt gtg aaa aca gct tta aca      2417
```

-continued

| | | | | | | | | | | | | | | |
|---|---|---|---|---|---|---|---|---|---|---|---|---|---|---|
| Gln | Gly | Trp | Asp | Trp | Ala | Gly | Glu | Ser | Gly | Val | Lys | Thr | Ala | Leu | Thr |
| | | | 575 | | | | | 580 | | | | | 585 | | |

```
att gaa gaa gca aac ggt tct aac gcg tta tca tgg gaa ttt gga tat    2465
Ile Glu Glu Ala Asn Gly Ser Asn Ala Leu Ser Trp Glu Phe Gly Tyr
            590                 595                 600 cca gaa gta aaa cct agt gat aac tgg gca aca gct cca cgt tta gat    2513
Pro Glu Val Lys Pro Ser Asp Asn Trp Ala Thr Ala Pro Arg Leu Asp
        605                 610                 615 ttc tgg aaa tct gac ttg gtt cgc ggt gag aat gat tat gta gct ttt    2561
Phe Trp Lys Ser Asp Leu Val Arg Gly Glu Asn Asp Tyr Val Ala Phe
    620                 625                 630 gat ttc tat cta gat cca gtt cgt gca aca gaa ggc gca atg aat atc    2609
Asp Phe Tyr Leu Asp Pro Val Arg Ala Thr Glu Gly Ala Met Asn Ile
635                 640                 645                 650 aat tta gta ttc cag cca cct act aac ggg tat tgg gta caa gca cca    2657
Asn Leu Val Phe Gln Pro Pro Thr Asn Gly Tyr Trp Val Gln Ala Pro
                655                 660                 665 aaa acg tat acg att aac ttt gat gaa tta gag gaa gcg aat caa gta    2705
Lys Thr Tyr Thr Ile Asn Phe Asp Glu Leu Glu Glu Ala Asn Gln Val
            670                 675                 680 aat ggt tta tat cac tat gaa gtg aaa att aac gta aga gat att aca    2753
Asn Gly Leu Tyr His Tyr Glu Val Lys Ile Asn Val Arg Asp Ile Thr
        685                 690                 695 aac att caa gat gac acg tta cta cgt aac atg atg atc att ttt gca    2801
Asn Ile Gln Asp Asp Thr Leu Leu Arg Asn Met Met Ile Ile Phe Ala
    700                 705                 710 gat gta gaa agt gac ttt gca ggg aga gtc ttt gta gat aat gtt cgt    2849
Asp Val Glu Ser Asp Phe Ala Gly Arg Val Phe Val Asp Asn Val Arg
715                 720                 725                 730 ttt gag ggg gct gct act act gag ccg gtt gaa cca gag cca gtt gat    2897
Phe Glu Gly Ala Ala Thr Thr Glu Pro Val Glu Pro Glu Pro Val Asp
                735                 740                 745 cct ggc gaa gag acg cca cct gtc gat gag aag gaa gcg aaa aaa gaa    2945
Pro Gly Glu Glu Thr Pro Pro Val Asp Glu Lys Glu Ala Lys Lys Glu
            750                 755                 760 caa aaa gaa gca gag aaa gaa gag aaa gaa gca gta aaa gaa gaa aag    2993
Gln Lys Glu Ala Glu Lys Glu Glu Lys Glu Ala Val Lys Glu Glu Lys
        765                 770                 775 aaa gaa gct aaa gaa gaa aag aaa gca gtc aaa aat gag gct aag aaa    3041
Lys Glu Ala Lys Glu Glu Lys Lys Ala Val Lys Asn Glu Ala Lys Lys
    780                 785                 790 aaa taatctatta aactagttat agggttatct aaaggtctga tgtagatctt        3094
Lys
795 ttagataacc ttttcttgc ataactggac acagagttgt tattaaagaa agtaag      3150

<210> SEQ ID NO 4
<211> LENGTH: 824
<212> TYPE: PRT
<213> ORGANISM: Bacillus sp. KSM-S237

<400> SEQUENCE: 4

Met Met Leu Arg Lys Lys Thr Lys Gln Leu Ile Ser Ser Ile Leu Ile
            -25                 -20                 -15

Leu Val Leu Leu Leu Ser Leu Phe Pro Ala Ala Leu Ala Ala Glu Gly
        -10                  -5                  -1    1

Asn Thr Arg Glu Asp Asn Phe Lys His Leu Leu Gly Asn Asp Asn Val
    5                   10                  15

Lys Arg Pro Ser Glu Ala Gly Ala Leu Gln Leu Gln Glu Val Asp Gly
20                  25                  30                  35
```

```
Gln Met Thr Leu Val Asp Gln His Gly Glu Lys Ile Gln Leu Arg Gly
                40                  45                  50
Met Ser Thr His Gly Leu Gln Trp Phe Pro Glu Ile Leu Asn Asp Asn
                55                  60                  65
Ala Tyr Lys Ala Leu Ser Asn Asp Trp Asp Ser Asn Met Ile Arg Leu
                70                  75                  80
Ala Met Tyr Val Gly Glu Asn Gly Tyr Ala Thr Asn Pro Glu Leu Ile
                85                  90                  95
Lys Gln Arg Val Ile Asp Gly Ile Glu Leu Ala Ile Glu Asn Asp Met
100                 105                 110                 115
Tyr Val Ile Val Asp Trp His Val His Ala Pro Gly Asp Pro Arg Asp
                120                 125                 130
Pro Val Tyr Ala Gly Ala Lys Asp Phe Phe Arg Glu Ile Ala Ala Leu
                135                 140                 145
Tyr Pro Asn Asn Pro His Ile Ile Tyr Glu Leu Ala Asn Glu Pro Ser
                150                 155                 160
Ser Asn Asn Asn Gly Gly Ala Gly Ile Pro Asn Asn Glu Glu Gly Trp
                165                 170                 175
Lys Ala Val Lys Glu Tyr Ala Asp Pro Ile Val Glu Met Leu Arg Lys
180                 185                 190                 195
Ser Gly Asn Ala Asp Asp Asn Ile Ile Ile Val Gly Ser Pro Asn Trp
                200                 205                 210
Ser Gln Arg Pro Asp Leu Ala Ala Asp Asn Pro Ile Asp Asp His His
                215                 220                 225
Thr Met Tyr Thr Val His Phe Tyr Thr Gly Ser His Ala Ala Ser Thr
                230                 235                 240
Glu Ser Tyr Pro Ser Glu Thr Pro Asn Ser Glu Arg Gly Asn Val Met
                245                 250                 255
Ser Asn Thr Arg Tyr Ala Leu Glu Asn Gly Val Ala Val Phe Ala Thr
260                 265                 270                 275
Glu Trp Gly Thr Ser Gln Ala Ser Gly Asp Gly Pro Tyr Phe Asp
                280                 285                 290
Glu Ala Asp Val Trp Ile Glu Phe Leu Asn Glu Asn Asn Ile Ser Trp
                295                 300                 305
Ala Asn Trp Ser Leu Thr Asn Lys Asn Glu Val Ser Gly Ala Phe Thr
                310                 315                 320
Pro Phe Glu Leu Gly Lys Ser Asn Ala Thr Asn Leu Asp Pro Gly Pro
                325                 330                 335
Asp His Val Trp Ala Pro Glu Glu Leu Ser Leu Ser Gly Glu Tyr Val
340                 345                 350                 355
Arg Ala Arg Ile Lys Gly Val Asn Tyr Glu Pro Ile Asp Arg Thr Lys
                360                 365                 370
Tyr Thr Lys Val Leu Trp Asp Phe Asn Asp Gly Thr Lys Gln Gly Phe
                375                 380                 385
Gly Val Asn Ser Asp Ser Pro Asn Lys Glu Leu Ile Ala Val Asp Asn
                390                 395                 400
Glu Asn Asn Thr Leu Lys Val Ser Gly Leu Asp Val Ser Asn Asp Val
                405                 410                 415
Ser Asp Gly Asn Phe Trp Ala Asn Ala Arg Leu Ser Ala Asn Gly Trp
420                 425                 430                 435
Gly Lys Ser Val Asp Ile Leu Gly Ala Glu Lys Leu Thr Met Asp Val
                440                 445                 450
Ile Val Asp Glu Pro Thr Thr Val Ala Ile Ala Ala Ile Pro Gln Ser
```

```
                    455                     460                     465

Ser Lys Ser Gly Trp Ala Asn Pro Glu Arg Ala Val Arg Val Asn Ala
        470                     475                     480

Glu Asp Phe Val Gln Gln Thr Asp Gly Lys Tyr Lys Ala Gly Leu Thr
    485                     490                     495

Ile Thr Gly Glu Asp Ala Pro Asn Leu Lys Asn Ile Ala Phe His Glu
500                     505                     510                 515

Glu Asp Asn Asn Met Asn Ile Ile Leu Phe Val Gly Thr Asp Ala
                    520                     525                     530

Ala Asp Val Ile Tyr Leu Asp Asn Ile Lys Val Ile Gly Thr Glu Val
            535                     540                     545

Glu Ile Pro Val Val His Asp Pro Lys Gly Glu Ala Val Leu Pro Ser
                550                     555                     560

Val Phe Glu Asp Gly Thr Arg Gln Gly Trp Asp Trp Ala Gly Glu Ser
            565                     570                     575

Gly Val Lys Thr Ala Leu Thr Ile Glu Glu Ala Asn Gly Ser Asn Ala
580                     585                     590                     595

Leu Ser Trp Glu Phe Gly Tyr Pro Glu Val Lys Pro Ser Asp Asn Trp
                    600                     605                     610

Ala Thr Ala Pro Arg Leu Asp Phe Trp Lys Ser Asp Leu Val Arg Gly
                615                     620                     625

Glu Asn Asp Tyr Val Ala Phe Asp Phe Tyr Leu Asp Pro Val Arg Ala
            630                     635                     640

Thr Glu Gly Ala Met Asn Ile Asn Leu Val Phe Gln Pro Pro Thr Asn
        645                     650                     655

Gly Tyr Trp Val Gln Ala Pro Lys Thr Tyr Thr Ile Asn Phe Asp Glu
660                     665                     670                     675

Leu Glu Glu Ala Asn Gln Val Asn Gly Leu Tyr His Tyr Glu Val Lys
                    680                     685                     690

Ile Asn Val Arg Asp Ile Thr Asn Ile Gln Asp Asp Thr Leu Leu Arg
                695                     700                     705

Asn Met Met Ile Ile Phe Ala Asp Val Glu Ser Asp Phe Ala Gly Arg
        710                     715                     720

Val Phe Val Asp Asn Val Arg Phe Glu Gly Ala Ala Thr Thr Glu Pro
    725                     730                     735

Val Glu Pro Glu Pro Val Asp Pro Gly Glu Glu Thr Pro Pro Val Asp
740                     745                     750                     755

Glu Lys Glu Ala Lys Lys Glu Gln Lys Glu Ala Glu Lys Glu Glu Lys
                    760                     765                     770

Glu Ala Val Lys Glu Glu Lys Lys Glu Ala Lys Glu Glu Lys Lys Ala
                775                     780                     785

Val Lys Asn Glu Ala Lys Lys Lys
        790                     795

<210> SEQ ID NO 5
<211> LENGTH: 3332
<212> TYPE: DNA
<213> ORGANISM: Bacillus sp. KSM-64
<220> FEATURE:
<221> NAME/KEY: CDS
<222> LOCATION: (610)..(3075)
<220> FEATURE:
<221> NAME/KEY: sig_peptide
<222> LOCATION: (610)..(696)
<220> FEATURE:
<221> NAME/KEY: mat_peptide
<222> LOCATION: (697)..(3075)
```

<400> SEQUENCE: 5

```
agtacttacc attttagagt caaaagatag aagccaagca ggatttgccg atgcaaccgg      60
cttatattta gagggaattt cttttttaaat tgaatacgga ataaaatcag gtaaacaggt    120
cctgatttta tttttttgaa ttttttttgag aactaaagat tgaaatagaa gtagaagaca   180
acggacataa gaaaattgta ttagttttaa ttatagaaaa cgcttttcta taattattta    240
tacctagaac gaaaatactg tttcgaaagc ggtttactat aaaaccttat attccggctc    300
tttttttaaa caggggggtga aaattcactc tagtattcta atttcaacat gctataataa    360
atttgtaaga cgcaatatac atcttttttt tatgatattt gtaagcggtt aaccttgtgc    420
tatatgccga tttaggaagg gggtagattg agtcaagtag tcataattta gataacttat    480
aagttgttga gaagcaggag agaatctggg ttactcacaa gttttttaaa acattatcga    540
aagcactttc ggttatgctt atgaatttag ctatttgatt caattacttt aataattttta   600
ggaggtaat atg atg tta aga aag aaa aca aag cag ttg att tct tcc att    651
          Met Met Leu Arg Lys Lys Thr Lys Gln Leu Ile Ser Ser Ile
                  -25                 -20 ctt att tta gtt tta ctt cta tct tta ttt ccg aca gct ctt gca gca    699
Leu Ile Leu Val Leu Leu Leu Ser Leu Phe Pro Thr Ala Leu Ala Ala
-15             -10                  -5             -1  1 gaa gga aac act cgt gaa gac aat ttt aaa cat tta tta ggt aat gac    747
Glu Gly Asn Thr Arg Glu Asp Asn Phe Lys His Leu Leu Gly Asn Asp
              5                  10                 15 aat gtt aaa cgc cct tct gag gct ggc gca tta caa tta caa gaa gtc    795
Asn Val Lys Arg Pro Ser Glu Ala Gly Ala Leu Gln Leu Gln Glu Val
         20                  25                  30 gat gga caa atg aca tta gta gat caa cat gga gaa aaa att caa tta    843
Asp Gly Gln Met Thr Leu Val Asp Gln His Gly Glu Lys Ile Gln Leu
     35                  40                  45 cgt gga atg agt aca cac gga tta caa tgg ttt cct gag atc ttg aat    891
Arg Gly Met Ser Thr His Gly Leu Gln Trp Phe Pro Glu Ile Leu Asn
50                  55                  60                  65 gat aac gca tac aaa gct ctt gct aac gat tgg gaa tca aat atg att    939
Asp Asn Ala Tyr Lys Ala Leu Ala Asn Asp Trp Glu Ser Asn Met Ile
                 70                  75                  80 cgt cta gct atg tat gtc ggt gaa aat ggc tat gct tca aat cca gag    987
Arg Leu Ala Met Tyr Val Gly Glu Asn Gly Tyr Ala Ser Asn Pro Glu
             85                  90                  95 tta att aaa agc aga gtc att aaa gga ata gat ctt gct att gaa aat   1035
Leu Ile Lys Ser Arg Val Ile Lys Gly Ile Asp Leu Ala Ile Glu Asn
        100                 105                 110 gac atg tat gtc atc gtt gat tgg cat gta cat gca cct ggt gat cct   1083
Asp Met Tyr Val Ile Val Asp Trp His Val His Ala Pro Gly Asp Pro
    115                 120                 125 aga gat ccc gtt tac gct gga gca gaa gat ttc ttt aga gat att gca   1131
Arg Asp Pro Val Tyr Ala Gly Ala Glu Asp Phe Phe Arg Asp Ile Ala
130                 135                 140                 145 gca tta tat cct aac aat cca cac att att tat gag tta gcg aat gag   1179
Ala Leu Tyr Pro Asn Asn Pro His Ile Ile Tyr Glu Leu Ala Asn Glu
                150                 155                 160 cca agt agt aac aat aat ggt gga gct ggg att cca aat aat gaa gaa   1227
Pro Ser Ser Asn Asn Asn Gly Gly Ala Gly Ile Pro Asn Asn Glu Glu
            165                 170                 175 ggt tgg aat gcg gta aaa gaa tac gct gat cca att gta gaa atg tta   1275
Gly Trp Asn Ala Val Lys Glu Tyr Ala Asp Pro Ile Val Glu Met Leu
        180                 185                 190 cgt gat agc ggg aac gca gat gac aat att atc att gtg ggt agt cca   1323
Arg Asp Ser Gly Asn Ala Asp Asp Asn Ile Ile Ile Val Gly Ser Pro
```

```
              195                 200                 205
aac tgg agt cag cgt cct gac tta gca gct gat aat cca att gat gat    1371
Asn Trp Ser Gln Arg Pro Asp Leu Ala Ala Asp Asn Pro Ile Asp Asp
210                 215                 220                 225 cac cat aca atg tat act gtt cac ttc tac act ggt tca cat gct gct    1419
His His Thr Met Tyr Thr Val His Phe Tyr Thr Gly Ser His Ala Ala
                230                 235                 240 tca act gaa agc tat ccg cct gaa act cct aac tct gaa aga gga aac    1467
Ser Thr Glu Ser Tyr Pro Pro Glu Thr Pro Asn Ser Glu Arg Gly Asn
            245                 250                 255 gta atg agt aac act cgt tat gcg tta gaa aac gga gta gca gta ttt    1515
Val Met Ser Asn Thr Arg Tyr Ala Leu Glu Asn Gly Val Ala Val Phe
        260                 265                 270 gca aca gag tgg gga act agc caa gca aat gga gat ggt ggt cct tac    1563
Ala Thr Glu Trp Gly Thr Ser Gln Ala Asn Gly Asp Gly Gly Pro Tyr
    275                 280                 285 ttt gat gaa gca gat gta tgg att gag ttt tta aat gaa aac aac att    1611
Phe Asp Glu Ala Asp Val Trp Ile Glu Phe Leu Asn Glu Asn Asn Ile
290                 295                 300                 305 agc tgg gct aac tgg tct tta acg aat aaa aat gaa gta tct ggt gca    1659
Ser Trp Ala Asn Trp Ser Leu Thr Asn Lys Asn Glu Val Ser Gly Ala
                310                 315                 320 ttt aca cca ttc gag tta ggt aag tct aac gca aca agt ctt gac cca    1707
Phe Thr Pro Phe Glu Leu Gly Lys Ser Asn Ala Thr Ser Leu Asp Pro
            325                 330                 335 ggg cca gac caa gta tgg gta cca gaa gag tta agt ctt tct gga gaa    1755
Gly Pro Asp Gln Val Trp Val Pro Glu Glu Leu Ser Leu Ser Gly Glu
        340                 345                 350 tat gta cgt gct cgt att aaa ggt gtg aac tat gag cca atc gac cgt    1803
Tyr Val Arg Ala Arg Ile Lys Gly Val Asn Tyr Glu Pro Ile Asp Arg
    355                 360                 365 aca aaa tac acg aaa gta ctt tgg gac ttt aat gat gga acg aag caa    1851
Thr Lys Tyr Thr Lys Val Leu Trp Asp Phe Asn Asp Gly Thr Lys Gln
370                 375                 380                 385 gga ttt gga gtg aat gga gat tct cca gtt gaa gat gta gtt att gag    1899
Gly Phe Gly Val Asn Gly Asp Ser Pro Val Glu Asp Val Val Ile Glu
                390                 395                 400 aat gaa gcg ggc gct tta aaa ctt tca gga tta gat gca agt aat gat    1947
Asn Glu Ala Gly Ala Leu Lys Leu Ser Gly Leu Asp Ala Ser Asn Asp
            405                 410                 415 gtt tct gaa ggt aat tac tgg gct aat gct cgt ctt tct gcc gac ggt    1995
Val Ser Glu Gly Asn Tyr Trp Ala Asn Ala Arg Leu Ser Ala Asp Gly
        420                 425                 430 tgg gga aaa agt gtt gat att tta ggt gct gaa aaa ctt act atg gat    2043
Trp Gly Lys Ser Val Asp Ile Leu Gly Ala Glu Lys Leu Thr Met Asp
    435                 440                 445 gtg att gtt gat gag ccg acc acg gta tca att gct gca att cca caa    2091
Val Ile Val Asp Glu Pro Thr Thr Val Ser Ile Ala Ala Ile Pro Gln
450                 455                 460                 465 ggg cca tca gcc aat tgg gtt aat cca aat cgt gca att aag gtt gag    2139
Gly Pro Ser Ala Asn Trp Val Asn Pro Asn Arg Ala Ile Lys Val Glu
                470                 475                 480 cca act aat ttc gta ccg tta gga gat aag ttt aaa gcg gaa tta act    2187
Pro Thr Asn Phe Val Pro Leu Gly Asp Lys Phe Lys Ala Glu Leu Thr
            485                 490                 495 ata act tca gct gac tct cca tcg tta gaa gct att gcg atg cat gct    2235
Ile Thr Ser Ala Asp Ser Pro Ser Leu Glu Ala Ile Ala Met His Ala
        500                 505                 510 gaa aat aac aac atc aac aac atc att ctt ttt gta gga act gaa ggt    2283
Glu Asn Asn Asn Ile Asn Asn Ile Ile Leu Phe Val Gly Thr Glu Gly
```

```
                515                 520                 525
gct gat gtt atc tat tta gat aac att aaa gta att gga aca gaa gtt      2331
Ala Asp Val Ile Tyr Leu Asp Asn Ile Lys Val Ile Gly Thr Glu Val
530                 535                 540                 545 gaa att cca gtt gtt cat gat cca aaa gga gaa gct gtt ctt cct tct      2379
Glu Ile Pro Val Val His Asp Pro Lys Gly Glu Ala Val Leu Pro Ser
                550                 555                 560 gtt ttt gaa gac ggt aca cgt caa ggt tgg gac tgg gct gga gag tct      2427
Val Phe Glu Asp Gly Thr Arg Gln Gly Trp Asp Trp Ala Gly Glu Ser
            565                 570                 575 ggt gtg aaa aca gct tta aca att gaa gaa gca aac ggt tct aac gcg      2475
Gly Val Lys Thr Ala Leu Thr Ile Glu Glu Ala Asn Gly Ser Asn Ala
        580                 585                 590 tta tca tgg gaa ttt gga tac cca gaa gta aaa cct agt gat aac tgg      2523
Leu Ser Trp Glu Phe Gly Tyr Pro Glu Val Lys Pro Ser Asp Asn Trp
    595                 600                 605 gca aca gct cca cgt tta gat ttc tgg aaa tct gac ttg gtt cgc ggt      2571
Ala Thr Ala Pro Arg Leu Asp Phe Trp Lys Ser Asp Leu Val Arg Gly
610                 615                 620                 625 gaa aat gat tat gta act ttt gat ttc tat cta gat cca gtt cgt gca      2619
Glu Asn Asp Tyr Val Thr Phe Asp Phe Tyr Leu Asp Pro Val Arg Ala
                630                 635                 640 aca gaa ggc gca atg aat atc aat tta gta ttc cag cca cct act aac      2667
Thr Glu Gly Ala Met Asn Ile Asn Leu Val Phe Gln Pro Pro Thr Asn
            645                 650                 655 ggg tat tgg gta caa gca cca aaa acg tat acg att aac ttt gat gaa      2715
Gly Tyr Trp Val Gln Ala Pro Lys Thr Tyr Thr Ile Asn Phe Asp Glu
        660                 665                 670 tta gag gaa gcg aat caa gta aat ggt tta tat cac tat gaa gtg aaa      2763
Leu Glu Glu Ala Asn Gln Val Asn Gly Leu Tyr His Tyr Glu Val Lys
    675                 680                 685 att aac gta aga gat att aca aac att caa gat gac acg tta cta cgt      2811
Ile Asn Val Arg Asp Ile Thr Asn Ile Gln Asp Asp Thr Leu Leu Arg
690                 695                 700                 705 aac atg atg atc att ttt gca gat gta gaa agt gac ttt gca ggg aga      2859
Asn Met Met Ile Ile Phe Ala Asp Val Glu Ser Asp Phe Ala Gly Arg
                710                 715                 720 gtc ttt gta gat aat gtt cgt ttt gag ggg gct gct act act gag ccg      2907
Val Phe Val Asp Asn Val Arg Phe Glu Gly Ala Ala Thr Thr Glu Pro
            725                 730                 735 gtt gaa cca gag cca gtt gat cct ggc gaa gag acg ccg cct gtc gat      2955
Val Glu Pro Glu Pro Val Asp Pro Gly Glu Glu Thr Pro Pro Val Asp
        740                 745                 750 gag aag gaa gcg aaa aaa gaa caa aaa gaa gca gag aaa gaa gag aaa      3003
Glu Lys Glu Ala Lys Lys Glu Gln Lys Glu Ala Glu Lys Glu Glu Lys
    755                 760                 765 gaa gca gta aaa gaa gaa aag aaa gaa gct aaa gaa gaa aag aaa gca      3051
Glu Ala Val Lys Glu Glu Lys Lys Glu Ala Lys Glu Glu Lys Lys Ala
770                 775                 780                 785 atc aaa aat gag gct acg aaa aaa taatctaata aactagttat agggttatct     3105
Ile Lys Asn Glu Ala Thr Lys Lys
                790 aaaggtctga tgcagatctt ttagataacc ttttttttgca taactggaca tagaatggtt   3165 attaaagaaa gcaaggtgtt tatacgatat taaaaaggta gcgattttaa attgaaacct    3225 ttaataatgt cttgtgatag aatgatgaag taatttaaga gggggaaacg aagtgaaaac    3285 ggaaatttct agtagaagaa aaacagacca agaaatactg caagctt                  3332

<210> SEQ ID NO 6
```

```
<211> LENGTH: 822
<212> TYPE: PRT
<213> ORGANISM: Bacillus sp. KSM-64

<400> SEQUENCE: 6
```

Met Met Leu Arg Lys Lys Thr Lys Gln Leu Ile Ser Ser Ile Leu Ile
            -25                 -20                 -15

Leu Val Leu Leu Leu Ser Leu Phe Pro Thr Ala Leu Ala Ala Glu Gly
            -10                  -5              -1   1

Asn Thr Arg Glu Asp Asn Phe Lys His Leu Leu Gly Asn Asp Asn Val
         5                  10                  15

Lys Arg Pro Ser Glu Ala Gly Ala Leu Gln Leu Gln Glu Val Asp Gly
 20                  25                  30                  35

Gln Met Thr Leu Val Asp Gln His Gly Glu Lys Ile Gln Leu Arg Gly
                 40                  45                  50

Met Ser Thr His Gly Leu Gln Trp Phe Pro Glu Ile Leu Asn Asp Asn
                 55                  60                  65

Ala Tyr Lys Ala Leu Ala Asn Asp Trp Glu Ser Asn Met Ile Arg Leu
         70                  75                  80

Ala Met Tyr Val Gly Glu Asn Gly Tyr Ala Ser Asn Pro Glu Leu Ile
         85                  90                  95

Lys Ser Arg Val Ile Lys Gly Ile Asp Leu Ala Ile Glu Asn Asp Met
100                 105                 110                 115

Tyr Val Ile Val Asp Trp His Val His Ala Pro Gly Asp Pro Arg Asp
                120                 125                 130

Pro Val Tyr Ala Gly Ala Glu Asp Phe Phe Arg Asp Ile Ala Ala Leu
                135                 140                 145

Tyr Pro Asn Asn Pro His Ile Ile Tyr Glu Leu Ala Asn Glu Pro Ser
                150                 155                 160

Ser Asn Asn Asn Gly Gly Ala Gly Ile Pro Asn Asn Glu Glu Gly Trp
                165                 170                 175

Asn Ala Val Lys Glu Tyr Ala Asp Pro Ile Val Glu Met Leu Arg Asp
180                 185                 190                 195

Ser Gly Asn Ala Asp Asp Asn Ile Ile Ile Val Gly Ser Pro Asn Trp
                200                 205                 210

Ser Gln Arg Pro Asp Leu Ala Ala Asp Asn Pro Ile Asp Asp His His
                215                 220                 225

Thr Met Tyr Thr Val His Phe Tyr Thr Gly Ser His Ala Ala Ser Thr
                230                 235                 240

Glu Ser Tyr Pro Pro Glu Thr Pro Asn Ser Glu Arg Gly Asn Val Met
245                 250                 255

Ser Asn Thr Arg Tyr Ala Leu Glu Asn Gly Val Ala Val Phe Ala Thr
260                 265                 270                 275

Glu Trp Gly Thr Ser Gln Ala Asn Gly Asp Gly Gly Pro Tyr Phe Asp
                280                 285                 290

Glu Ala Asp Val Trp Ile Glu Phe Leu Asn Glu Asn Asn Ile Ser Trp
                295                 300                 305

Ala Asn Trp Ser Leu Thr Asn Lys Asn Glu Val Ser Gly Ala Phe Thr
                310                 315                 320

Pro Phe Glu Leu Gly Lys Ser Asn Ala Thr Ser Leu Asp Pro Gly Pro
325                 330                 335

Asp Gln Val Trp Val Pro Glu Glu Leu Ser Leu Ser Gly Glu Tyr Val
340                 345                 350                 355

Arg Ala Arg Ile Lys Gly Val Asn Tyr Glu Pro Ile Asp Arg Thr Lys
                360                 365                 370

```
Tyr Thr Lys Val Leu Trp Asp Phe Asn Asp Gly Thr Lys Gln Gly Phe
            375                 380                 385

Gly Val Asn Gly Asp Ser Pro Val Glu Asp Val Val Ile Glu Asn Glu
        390                 395                 400

Ala Gly Ala Leu Lys Leu Ser Gly Leu Asp Ala Ser Asn Asp Val Ser
405                 410                 415

Glu Gly Asn Tyr Trp Ala Asn Ala Arg Leu Ser Ala Asp Gly Trp Gly
420                 425                 430                 435

Lys Ser Val Asp Ile Leu Gly Ala Glu Lys Leu Thr Met Asp Val Ile
                440                 445                 450

Val Asp Glu Pro Thr Thr Val Ser Ile Ala Ala Ile Pro Gln Gly Pro
                455                 460                 465

Ser Ala Asn Trp Val Asn Pro Asn Arg Ala Ile Lys Val Glu Pro Thr
            470                 475                 480

Asn Phe Val Pro Leu Gly Asp Lys Phe Lys Ala Glu Leu Thr Ile Thr
485                 490                 495

Ser Ala Asp Ser Pro Ser Leu Glu Ala Ile Ala Met His Ala Glu Asn
500                 505                 510                 515

Asn Asn Ile Asn Asn Ile Ile Leu Phe Val Gly Thr Glu Gly Ala Asp
                520                 525                 530

Val Ile Tyr Leu Asp Asn Ile Lys Val Ile Gly Thr Glu Val Glu Ile
                535                 540                 545

Pro Val Val His Asp Pro Lys Gly Glu Ala Val Leu Pro Ser Val Phe
                550                 555                 560

Glu Asp Gly Thr Arg Gln Gly Trp Asp Trp Ala Gly Glu Ser Gly Val
565                 570                 575

Lys Thr Ala Leu Thr Ile Glu Glu Ala Asn Gly Ser Asn Ala Leu Ser
580                 585                 590                 595

Trp Glu Phe Gly Tyr Pro Glu Val Lys Pro Ser Asp Asn Trp Ala Thr
                600                 605                 610

Ala Pro Arg Leu Asp Phe Trp Lys Ser Asp Leu Val Arg Gly Glu Asn
            615                 620                 625

Asp Tyr Val Thr Phe Asp Phe Tyr Leu Asp Pro Val Arg Ala Thr Glu
            630                 635                 640

Gly Ala Met Asn Ile Asn Leu Val Phe Gln Pro Pro Thr Asn Gly Tyr
            645                 650                 655

Trp Val Gln Ala Pro Lys Thr Tyr Thr Ile Asn Phe Asp Glu Leu Glu
660                 665                 670                 675

Glu Ala Asn Gln Val Asn Gly Leu Tyr His Tyr Glu Val Lys Ile Asn
                680                 685                 690

Val Arg Asp Ile Thr Asn Ile Gln Asp Asp Thr Leu Leu Arg Asn Met
            695                 700                 705

Met Ile Ile Phe Ala Asp Val Glu Ser Asp Phe Ala Gly Arg Val Phe
            710                 715                 720

Val Asp Asn Val Arg Phe Glu Gly Ala Ala Thr Thr Glu Pro Val Glu
            725                 730                 735

Pro Glu Pro Val Asp Pro Gly Glu Glu Thr Pro Pro Val Asp Glu Lys
740                 745                 750                 755

Glu Ala Lys Lys Glu Gln Lys Glu Ala Glu Lys Glu Lys Glu Lys Ala
                760                 765                 770

Val Lys Glu Glu Lys Lys Glu Ala Lys Glu Glu Lys Lys Ala Ile Lys
            775                 780                 785

Asn Glu Ala Thr Lys Lys
```

<210> SEQ ID NO 7
<211> LENGTH: 230
<212> TYPE: DNA
<213> ORGANISM: Bacillus subtilis

<400> SEQUENCE: 7
gttagtcgag atcgaagtta ttgcactggt gaaataataa gaaaagtgat tctgggagag    60
ccgggatcac ttttttattt accttatgcc cgaaatgaaa gctttatgac ctaattgtgt   120
aactatatcc tattttttca aaaatatttt taaaaacgag caggatttca gaaaaaatcg   180
tggaattgat acactaatgc ttttatatag ggaaaaggtg gtgaactact                230

<210> SEQ ID NO 8
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of Bacillus subtilis
      gene, spoVG

<400> SEQUENCE: 8
gttagtcgag atcgaagtta                                                 20

<210> SEQ ID NO 9
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of Bacillus subtilis
      gene, spoVG

<400> SEQUENCE: 9
agtagttcac cacctttttcc                                                20

<210> SEQ ID NO 10
<211> LENGTH: 43
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      secY and a 5'-portion designed from the nucleotide sequence of
      5'-flanking region of Bacillus subtilis gene, spoVG

<400> SEQUENCE: 10
ggaaaaggtg gtgaactact atgttgttta aacaatctc caa                        43

<210> SEQ ID NO 11
<211> LENGTH: 40
<212> TYPE: DNA
<213> ORGANISM: Artificial sequence
<220> FEATURE:
<223> OTHER INFORMATION: Oligonucleotide as PCR primer with a 3'-
      portion designed from the nucleotide sequence of Bacillus subtilis
      gene, secY and a 5'-portion designed from the nucleotide sequence
      of chloramphenicol resistant gene

<400> SEQUENCE: 11
atgggtgctt tagttgaaga ctagttttc ataaatccac                            40

<210> SEQ ID NO 12
<211> LENGTH: 19
<212> TYPE: DNA

```
<213> ORGANISM: Artificial sequence
<220> FEATURE:
<223> OTHER INFORMATION: Oligonucleotide as forward PCR primer for
      amplification of chloramphenicol resistant gene

<400> SEQUENCE: 12
caactaaagc acccattag                                                  19

<210> SEQ ID NO 13
<211> LENGTH: 18
<212> TYPE: DNA
<213> ORGANISM: Artificial sequence
<220> FEATURE:
<223> OTHER INFORMATION: Oligonucleotide as reverse PCR primer for
      amplification of chloramphenicol resistant gene

<400> SEQUENCE: 13
cttcaactaa cggggcag                                                   18

<210> SEQ ID NO 14
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of Bacillus subtilis
      gene, spoVG

<400> SEQUENCE: 14
taagaaaagt gattctggga                                                 20

<210> SEQ ID NO 15
<211> LENGTH: 21
<212> TYPE: DNA
<213> ORGANISM: Artificial sequence
<220> FEATURE:
<223> OTHER INFORMATION: Oligonucleotide as reverse PCR primer for
      amplification of chloramphenicol resistant gene

<400> SEQUENCE: 15
ctcatattat aaaagccagt c                                               21

<210> SEQ ID NO 16
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of Bacillus subtilis gene, amyE

<400> SEQUENCE: 16
ggagtgtcaa gaatgtttgc                                                 20

<210> SEQ ID NO 17
<211> LENGTH: 40
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      amyE and a 5'-portion designed from the nucleotide sequence of
      5'-flanking region of Bacillus subtilis gene, spoVG

<400> SEQUENCE: 17
tcccagaatc acttttctta atcatcgctc atccatgtcg                           40

<210> SEQ ID NO 18
<211> LENGTH: 41
```

```
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      amyE and a 5'-portion designed from the nucleotide sequence of
      chloramphenicol resistant gene

<400> SEQUENCE: 18
gactggcttt tataatatga ggtttaggct gggcggtgat a                 41

<210> SEQ ID NO 19
<211> LENGTH: 18
<212> TYPE: DNA
<213> ORGANISM: Artificial sequence
<220> FEATURE:
<223> OTHER INFORMATION: Oligonucleotide as PCR primer designed from the
      nucleotide sequence of Bacillus subtilis gene, amyE

<400> SEQUENCE: 19
tcaatgggga agagaacc                                          18

<210> SEQ ID NO 20
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of Bacillus subtilis gene, amyE

<400> SEQUENCE: 20
tcaaaacctc tttactgccg                                        20

<210> SEQ ID NO 21
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of Bacillus subtilis gene, amyE

<400> SEQUENCE: 21
cacgtaatca aagccaggct                                        20

<210> SEQ ID NO 22
<211> LENGTH: 37
<212> TYPE: DNA
<213> ORGANISM: Artificial sequence
<220> FEATURE:
<223> OTHER INFORMATION: Oligonucleotide as PCR primer designed from
      nucleotide sequence of the upstream region of the alkaline
      cellulase gene in Bacillus sp. KSM-S237 with a insertion of the
      BamHI restriction site at the 5'-end

<400> SEQUENCE: 22
ttgcggatcc aacaggctta tatttagagg aaatttc                     37

<210> SEQ ID NO 23
<211> LENGTH: 36
<212> TYPE: DNA
<213> ORGANISM: Artificial sequence
<220> FEATURE:
<223> OTHER INFORMATION: Oligonucleotide as PCR primer designed from
      nucleotide sequence of the downstream region of the alkaline
      cellulase gene in Bacillus sp. KSM-S237 with a insertion of the
      BamHI restriction site at the 5'-end

<400> SEQUENCE: 23
ttgcggatcc aacaactctg tgtccagtta tgcaag                      36
```

<210> SEQ ID NO 24
<211> LENGTH: 40
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      secE and a 5'-portion designed from the nucleotide sequence of
      5'-flanking region of Bacillus subtilis gene, secY

<400> SEQUENCE: 24
gtggatttat gaaaaactag ttgtggaggt cttttacatg                              40

<210> SEQ ID NO 25
<211> LENGTH: 40
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      secE and a 5'-portion designed from the nucleotide sequence of
      neomycin resistant gene

<400> SEQUENCE: 25
tattttataa actcattccc cattattcaa ctattaaacg                              40

<210> SEQ ID NO 26
<211> LENGTH: 40
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      amyE and a 5'-portion designed from the nucleotide sequence of
      neomycin resistant gene

<400> SEQUENCE: 26
tgacctctaa taattgttaa gtttaggctg ggcggtgata                              40

<210> SEQ ID NO 27
<211> LENGTH: 19
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of plasmid pUB110 gene,
      repU

<400> SEQUENCE: 27
gggaatgagt ttataaaat                                                    19

<210> SEQ ID NO 28
<211> LENGTH: 41
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of plasmid pUB110 gene, repU
      and a 5'-portion designed from the nucleotide sequence of neomycin
      resistant gene

<400> SEQUENCE: 28
ttcctaagca tcatggtctc acttttccac tttttgtctt g                           41

<210> SEQ ID NO 29
<211> LENGTH: 39
<212> TYPE: DNA
<213> ORGANISM: Artificial sequence

```
<220> FEATURE:
<223> OTHER INFORMATION: Oligonucleotide as PCR primer with a 3'-portion
      designed from the nucleotide sequence of neomycin resistant gene
      and a 5'-portion designed from the nucleotide sequence of plasmid
      pUB110 gene, repU

<400> SEQUENCE: 29
gtgagaccat gatgcttagg aagacgagtt attaatagc                          39

<210> SEQ ID NO 30
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of 5'-flanking region of neomycin resistant
      gene

<400> SEQUENCE: 30
ttaacaatta ttagaggtca                                               20

<210> SEQ ID NO 31
<211> LENGTH: 20
<212> TYPE: DNA
<213> ORGANISM: Artificial sequence
<220> FEATURE:
<223> OTHER INFORMATION: Oligonucleotide as PCR primer designed from the
      nucleotide sequence of Bacillus subtilis gene, secY

<400> SEQUENCE: 31
ttgtttaaaa caatctccaa                                               20

<210> SEQ ID NO 32
<211> LENGTH: 40
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      secG and a 5'-portion designed from the nucleotide sequence of
      5'-flanking region of Bacillus subtilis gene, spoVG

<400> SEQUENCE: 32
ggaaaaggtg gtgaactact tgagtctgga ggtgtatggg                         40

<210> SEQ ID NO 33
<211> LENGTH: 40
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      secY and a 5'-portion designed from the nucleotide sequence of
      neomycin resistant gene

<400> SEQUENCE: 33
tattttataa actcattccc ccctatagga tataagcaag                         40

<210> SEQ ID NO 34
<211> LENGTH: 25
<212> TYPE: DNA
<213> ORGANISM: Artificial sequence
<220> FEATURE:
<223> OTHER INFORMATION: Oligonucleotide as PCR primer designed from
      nucleotide sequence of the upstream region of the alkaline
      cellulase gene in Bacillus sp. KSM-S237 with a insertion of the
      BamHI restriction site at the 5'-end

<400> SEQUENCE: 34
```
cccggatcca acaggcttat attta                                            25

<210> SEQ ID NO 35
<211> LENGTH: 29
<212> TYPE: DNA
<213> ORGANISM: Artificial sequence
<220> FEATURE:
<223> OTHER INFORMATION: Oligonucleotide as PCR primer; its 3'-portion
      designed from nucleotide sequence of the alkaline cellulase gene
      in Bacillus sp. KSM-S237 and its 5'-portion designed from
      nucleotide sequence of the alkaline amylase gene in Bacillus sp.
      KSM-K38

<400> SEQUENCE: 35
ttcaatccat ctgctgcaag agctgccgg                                        29

<210> SEQ ID NO 36
<211> LENGTH: 30
<212> TYPE: DNA
<213> ORGANISM: Artificial sequence
<220> FEATURE:
<223> OTHER INFORMATION: Oligonucleotide as PCR primer; its 3'-portion
      designed from nucleotide sequence of the alkaline amylase gene in
      Bacillus sp. KSM-K38 and its 5'-portion designed from nucleotide
      sequence of the alkaline cellulase gene in Bacillus sp. KSM-S237

<400> SEQUENCE: 36
gctcttgcag cagatggatt gaacggtacg                                       30

<210> SEQ ID NO 37
<211> LENGTH: 30
<212> TYPE: DNA
<213> ORGANISM: Artificial sequence
<220> FEATURE:
<223> OTHER INFORMATION: Oligonucleotide as PCR primer designed from
      nucleotide sequence of the downstream region of the alkaline
      amylase gene in Bacillus sp. KSM-K38 with a insertion of the XbaI
      restriction site at the 5'-end

<400> SEQUENCE: 37
ttggtctaga ccccaagctt caaagtcgta                                       30

<210> SEQ ID NO 38
<211> LENGTH: 40
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      secG and a 5'-portion designed from the nucleotide sequence of
      5'-flanking region of Bacillus subtilis gene, secY

<400> SEQUENCE: 38
gtggatttat gaaaaactag tgagtctgga ggtgtatggg                            40

<210> SEQ ID NO 39
<211> LENGTH: 40
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      secY and a 5'-portion designed from the nucleotide sequence of
      neomycin resistant gene

<400> SEQUENCE: 39
tattttataa actcattccc ccctatagga tataagcaag                            40

<210> SEQ ID NO 40

```
<211> LENGTH: 48
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      secE and a 5'-portion designed from the nucleotide sequence of
      5'-flanking region of Bacillus subtilis gene, spoVG

<400> SEQUENCE: 40
ggaaaaggtg gtgaactact atgcgtatta tgaaattctt taaagatg                48

<210> SEQ ID NO 41
<211> LENGTH: 48
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus subtilis gene,
      secE and a 5'-portion designed from the nucleotide sequence of
      chloramphenicol resistant gene

<400> SEQUENCE: 41
atgggtgctt tagttgaaga ttattcaact attaaacgaa ttaattga                48

<210> SEQ ID NO 42
<211> LENGTH: 1441
<212> TYPE: DNA
<213> ORGANISM: Bacillus clausii KSM-K16
<220> FEATURE:
<221> NAME/KEY: CDS
<222> LOCATION: (164)..(1303)

<400> SEQUENCE: 42
tggtagcttt ccccacttga aaccgtttta atcaaaaaac aaagtgggaa aattctgtta        60
acttaatgtt aataattgtt tcccaatagg caaatctttc taactttgat acgtttaaac       120
taccagcttg acgagttgg gataaaagtg aggagggaac cga atg aag aaa ccg          175
                                                 Met Lys Lys Pro
                                                  1 ttg ggg aaa att gtc gca agc acc gca cta ctc att tct gtt gct ttt         223
Leu Gly Lys Ile Val Ala Ser Thr Ala Leu Leu Ile Ser Val Ala Phe
 5                  10                  15                  20 agt tca tcg atc gca tcg gct gct gag gaa gca aaa gaa aaa tat tta         271
Ser Ser Ser Ile Ala Ser Ala Ala Glu Glu Ala Lys Glu Lys Tyr Leu
             25                  30                  35 att ggc ttt aat gag cag gaa gca gtt agt gag ttt gta gag caa ata         319
Ile Gly Phe Asn Glu Gln Glu Ala Val Ser Glu Phe Val Glu Gln Ile
         40                  45                  50 gag gca aat gac gat gtc gcg att ctc tct gag gaa gag gaa gtc gaa         367
Glu Ala Asn Asp Asp Val Ala Ile Leu Ser Glu Glu Glu Glu Val Glu
     55                  60                  65 att gaa ttg ctt cat gag ttt gaa acg att cct gtt tta tct gtt gag         415
Ile Glu Leu Leu His Glu Phe Glu Thr Ile Pro Val Leu Ser Val Glu
 70                  75                  80 tta agt cca gaa gat gtg gac gcg ctt gag ctc gat cca acg att tcg         463
Leu Ser Pro Glu Asp Val Asp Ala Leu Glu Leu Asp Pro Thr Ile Ser
 85                  90                  95                 100 tat att gaa gag gat gca gaa gta acg aca atg gcg caa tca gtg cca         511
Tyr Ile Glu Glu Asp Ala Glu Val Thr Thr Met Ala Gln Ser Val Pro
             105                 110                 115 tgg gga att agc cgt gta caa gcc cca gct gcc cat aac cgt gga ttg         559
Trp Gly Ile Ser Arg Val Gln Ala Pro Ala Ala His Asn Arg Gly Leu
         120                 125                 130 aca ggt tct ggt gta aaa gtt gct gtc ctc gat acg ggt att tcc acc         607
Thr Gly Ser Gly Val Lys Val Ala Val Leu Asp Thr Gly Ile Ser Thr
```

|     |     |     |     |     |     |     |     |     |     |     |     |     |     |     |
| --- | --- | --- | --- | --- | --- | --- | --- | --- | --- | --- | --- | --- | --- | --- |
| Thr | Gly | Ser | Gly | Val | Lys | Val | Ala | Val | Leu | Asp | Thr | Gly | Ile | Ser | Thr |
|     |     | 135 |     |     |     | 140 |     |     |     |     | 145 |     |     |     |     |

```
cat cca gac tta aat att cgc ggt ggt gct agc ttt gtg cca gga gaa       655
His Pro Asp Leu Asn Ile Arg Gly Gly Ala Ser Phe Val Pro Gly Glu
    150             155                 160 cca tcc act caa gat gga aat gga cat ggc acg cat gtg gca ggg acg       703
Pro Ser Thr Gln Asp Gly Asn Gly His Gly Thr His Val Ala Gly Thr
165             170                 175                 180 att gct gct tta aac aat tcg att ggc gtt ctg ggc gta gca ccg agc       751
Ile Ala Ala Leu Asn Asn Ser Ile Gly Val Leu Gly Val Ala Pro Ser
                185                 190                 195 gcg gaa cta tac gct gta aaa gta tta ggc gcg agc ggt tca ggt tcg       799
Ala Glu Leu Tyr Ala Val Lys Val Leu Gly Ala Ser Gly Ser Gly Ser
            200                 205                 210 gtc agc tcg att gcc caa gga ttg gaa tgg gca ggg aac aat ggc atg       847
Val Ser Ser Ile Ala Gln Gly Leu Glu Trp Ala Gly Asn Asn Gly Met
        215                 220                 225 cac gtt gcg aat ttg agt tta gga agc ccg tcg ccg agt gca aca ctt       895
His Val Ala Asn Leu Ser Leu Gly Ser Pro Ser Pro Ser Ala Thr Leu
    230                 235                 240 gag caa gct gtt aat agc gct act tct aga ggc gtt ctt gtc gta gca       943
Glu Gln Ala Val Asn Ser Ala Thr Ser Arg Gly Val Leu Val Val Ala
245                 250                 255                 260 gca tct ggt aat tca ggt gca ggc tca atc agc tat ccg gcc cgt tat       991
Ala Ser Gly Asn Ser Gly Ala Gly Ser Ile Ser Tyr Pro Ala Arg Tyr
                265                 270                 275 gcg aac gca atg gca gtc gga gcg act gac caa aac aac aac cgc gct      1039
Ala Asn Ala Met Ala Val Gly Ala Thr Asp Gln Asn Asn Asn Arg Ala
            280                 285                 290 agc ttt tca cag tat gga gct ggg ctt gac att gtc gcg cca ggt gtc      1087
Ser Phe Ser Gln Tyr Gly Ala Gly Leu Asp Ile Val Ala Pro Gly Val
        295                 300                 305 aat gtg cag agc aca tac cca ggt tca aca tat gcc agc tta aac ggt      1135
Asn Val Gln Ser Thr Tyr Pro Gly Ser Thr Tyr Ala Ser Leu Asn Gly
    310                 315                 320 aca tcg atg gct act cct cat gtt gca ggt gta gca gcc ctt gtt aaa      1183
Thr Ser Met Ala Thr Pro His Val Ala Gly Val Ala Ala Leu Val Lys
325                 330                 335                 340 caa aag aat cca tct tgg tcc aat gta caa atc cgc aat cat cta aag      1231
Gln Lys Asn Pro Ser Trp Ser Asn Val Gln Ile Arg Asn His Leu Lys
                345                 350                 355 aat acg gca acg ggt tta gga aac acg aac ttg tat gga agc ggg ctt      1279
Asn Thr Ala Thr Gly Leu Gly Asn Thr Asn Leu Tyr Gly Ser Gly Leu
            360                 365                 370 gtc aat gca gaa gcg gca aca cgc taatcaataa taataacgct gtgtgcttta     1333
Val Asn Ala Glu Ala Ala Thr Arg
        375                 380 agcacacagc gtttttttagt gtgtatgaat cgaaaaagag aaatagatcg ctgatttcaa   1393
aaagcgagcg taagggcta ttgaagctct ttacgcttgc aggatttg                  1441
```

<210> SEQ ID NO 43
<211> LENGTH: 380
<212> TYPE: PRT
<213> ORGANISM: Bacillus clausii KSM-K16

<400> SEQUENCE: 43

|     |     |     |     |     |     |     |     |     |     |     |     |     |     |     |
| --- | --- | --- | --- | --- | --- | --- | --- | --- | --- | --- | --- | --- | --- | --- |
| Met | Lys | Lys | Pro | Leu | Gly | Lys | Ile | Val | Ala | Ser | Thr | Ala | Leu | Leu | Ile |
| 1   |     |     |     | 5   |     |     |     |     | 10  |     |     |     |     | 15  |     |
| Ser | Val | Ala | Phe | Ser | Ser | Ser | Ile | Ala | Ser | Ala | Ala | Glu | Glu | Ala | Lys |
|     |     | 20  |     |     |     |     | 25  |     |     |     |     | 30  |     |     |     |

Glu Lys Tyr Leu Ile Gly Phe Asn Glu Gln Glu Ala Val Ser Glu Phe
        35                  40                  45

Val Glu Gln Ile Glu Ala Asn Asp Val Ala Ile Leu Ser Glu Glu
 50                  55                  60

Glu Glu Val Glu Ile Leu Leu His Glu Phe Glu Thr Ile Pro Val
 65                  70                  75                  80

Leu Ser Val Glu Leu Ser Pro Glu Asp Val Asp Ala Leu Glu Leu Asp
                85                  90                  95

Pro Thr Ile Ser Tyr Ile Glu Glu Asp Ala Glu Val Thr Thr Met Ala
                100                 105                 110

Gln Ser Val Pro Trp Gly Ile Ser Arg Val Gln Ala Pro Ala Ala His
                115                 120                 125

Asn Arg Gly Leu Thr Gly Ser Gly Val Lys Val Ala Val Leu Asp Thr
130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
                180                 185                 190

Val Ala Pro Ser Ala Glu Leu Tyr Ala Val Lys Val Leu Gly Ala Ser
                195                 200                 205

Gly Ser Gly Ser Val Ser Ser Ile Ala Gln Gly Leu Glu Trp Ala Gly
210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Gly Ser Ile Ser Tyr
                260                 265                 270

Pro Ala Arg Tyr Ala Asn Ala Met Ala Val Gly Ala Thr Asp Gln Asn
                275                 280                 285

Asn Asn Arg Ala Ser Phe Ser Gln Tyr Gly Ala Gly Leu Asp Ile Val
290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Val Ala
                325                 330                 335

Ala Leu Val Lys Gln Lys Asn Pro Ser Trp Ser Asn Val Gln Ile Arg
                340                 345                 350

Asn His Leu Lys Asn Thr Ala Thr Gly Leu Gly Asn Thr Asn Leu Tyr
                355                 360                 365

Gly Ser Gly Leu Val Asn Ala Glu Ala Ala Thr Arg
370                 375                 380

<210> SEQ ID NO 44
<211> LENGTH: 46
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus clausii KSM-K16
      alkaline protease gene and a 5'-portion designed from the
      nucleotide sequence of Bacillus sp. KSM-S237 alkaline cellulase
      gene

<400> SEQUENCE: 44

```
actttaaaaa tatttaggag gtaatatgaa gaaaccgttg gggaaa                     46

<210> SEQ ID NO 45
<211> LENGTH: 32
<212> TYPE: DNA
<213> ORGANISM: Artificial sequence
<220> FEATURE:
<223> OTHER INFORMATION: Oligonucleotide as PCR primer designed from the
      nucleotide sequence of downstream region of Bacillus clausii
      KSM-K16 alkaline protease gene

<400> SEQUENCE: 45
gggagatctt cagcgatcta tttctctttt tc                                    32

<210> SEQ ID NO 46
<211> LENGTH: 25
<212> TYPE: DNA
<213> ORGANISM: Artificial sequence
<220> FEATURE:
<223> OTHER INFORMATION: Oligonucleotide as PCR primer designed from the
      nucleotide sequence of upstream region of Bacillus sp. KSM-S237
      alkaline cellulase gene

<400> SEQUENCE: 46
cccggatcca acaggcttat attta                                            25

<210> SEQ ID NO 47
<211> LENGTH: 46
<212> TYPE: DNA
<213> ORGANISM: Artificial sequence
<220> FEATURE:
<223> OTHER INFORMATION: Oligonucleotide as PCR primer with a 3'-portion
      designed from the nucleotide sequence of Bacillus sp. KSM-S237
      alkaline cellulase gene and a 5'-portion designed from the
      nucleotide sequence of Bacillus clausii KSM-K16 alkaline protease
      gene

<400> SEQUENCE: 47
tttccccaac ggtttcttca tattacctcc taaatatttt taaagt                     46
```